United States Patent
Iguchi et al.

(10) Patent No.: US 10,151,693 B2
(45) Date of Patent: Dec. 11, 2018

(54) PHOTOELECTRIC SMOKE SENSOR

(71) Applicant: FENWAL CONTROLS OF JAPAN, LTD., Tokyo (JP)

(72) Inventors: Masao Iguchi, Tokyo (JP); Tadayuki Shibuya, Tokyo (JP); Kanji Numao, Tokyo (JP); Shintaro Masumoto, Tokyo (JP)

(73) Assignee: FENWAL CONTROLS OF JAPAN, LTD., Tokyo (JP)

( * ) Notice: Subject to any disclaimer, the term of this patent is extended or adjusted under 35 U.S.C. 154(b) by 0 days.

(21) Appl. No.: 15/902,010

(22) Filed: Feb. 22, 2018

(65) Prior Publication Data
US 2018/0180540 A1 Jun. 28, 2018

Related U.S. Application Data

(63) Continuation of application No. PCT/JP2016/063244, filed on Apr. 27, 2016.

(30) Foreign Application Priority Data

Aug. 25, 2015 (JP) ................. 2015-165757

(51) Int. Cl.
*G01N 21/53* (2006.01)
*G08B 17/10* (2006.01)
*G08B 17/107* (2006.01)

(52) U.S. Cl.
CPC ............. *G01N 21/53* (2013.01); *G08B 17/10* (2013.01); *G08B 17/107* (2013.01); *G01N 2201/0227* (2013.01)

(58) Field of Classification Search
CPC .... G08B 17/117; G08B 17/107; G08B 17/10; G01N 15/0656; G01N 21/53; G01N 2201/0227

See application file for complete search history.

(56) References Cited

U.S. PATENT DOCUMENTS 3,767,917 A 10/1973 Lampart et al.
4,396,840 A 8/1983 Araki et al.
(Continued)

FOREIGN PATENT DOCUMENTS

CN 2199567 Y 5/1995
CN 201374114 Y 12/2009
(Continued)

OTHER PUBLICATIONS

Office Action dated Jan. 3, 2017 by the Taiwanese Intellectual Property Office in connection with related Taiwanese Patent Application No. TW 105113304 including English language translation.
(Continued)

*Primary Examiner* — Michael P Stafira

(74) *Attorney, Agent, or Firm* — John P. White; Cooper & Dunahm LLP

(57) ABSTRACT

A photoelectric smoke sensor includes a housing having a circuit accommodation chamber, an inflow chamber provided in the housing, a light emitting portion provided in the inflow chamber, and a light receiving portion provided in the inflow chamber. The light emitting portion includes a first light and a first support portion surrounding the first light guide. The light receiving portion includes a second light guide and guiding the light to the light receiving element and a second support portion surrounding the second light guide. The first support portion and the second support portion are configured to prevent escape of a flame from the circuit accommodation chamber to the inflow chamber.

12 Claims, 17 Drawing Sheets

(56) References Cited

U.S. PATENT DOCUMENTS

| | | | |
|---|---|---|---|
| 4,539,556 A | 9/1985 | Dederich et al. | |
| 4,642,471 A * | 2/1987 | Guttinger | G08B 17/107 |
| | | | 250/564 |
| 4,786,811 A | 11/1988 | Sasaki | |
| 4,851,819 A | 7/1989 | Kawai et al. | |
| 4,897,634 A | 1/1990 | Sawa et al. | |
| 5,021,677 A | 6/1991 | Igarashi et al. | |
| 5,486,816 A | 1/1996 | Ariga et al. | |
| 5,670,947 A | 9/1997 | Nagashima | |
| 6,737,977 B2 | 5/2004 | Nishikawa et al. | |
| 6,756,905 B2 | 6/2004 | Rattman et al. | |
| 6,778,091 B2 | 8/2004 | Qualey, III et al. | |
| 7,697,140 B2 | 4/2010 | Iguchi et al. | |
| 9,157,854 B2 | 10/2015 | Matsukuma | |
| 9,514,623 B1 | 12/2016 | Urrutia et al. | |
| 9,652,957 B2 | 5/2017 | Urrutia et al. | |
| 9,685,058 B2 | 6/2017 | Schmidt et al. | |
| 2011/0068936 A1 | 3/2011 | Shimada et al. | |
| 2016/0305874 A1 | 10/2016 | Iguchi et al. | |

FOREIGN PATENT DOCUMENTS

| | | |
|---|---|---|
| DE | 10 2013 213 721 A1 | 5/2014 |
| FR | 2 666 163 A1 | 2/1992 |
| JP | 56-53296 U | 7/1981 |
| JP | 56-94495 A | 7/1981 |
| JP | 58-129145 U | 9/1983 |
| JP | 63-8538 A | 1/1988 |
| JP | 63-20050 U | 2/1988 |
| JP | 11-167683 A | 6/1999 |
| JP | 11-167686 A | 6/1999 |
| JP | 11-175860 A | 7/1999 |
| JP | 11-312281 A | 11/1999 |
| JP | 2002-358583 A | 12/2002 |
| JP | 2003-141654 A | 5/2003 |
| JP | 2007-127594 | 5/2007 |
| JP | 3938750 B2 | 6/2007 |
| KR | 10-1236239 B1 | 5/2013 |
| TW | 201027466 A1 | 7/2010 |
| WO | WO 2016/009460 A1 | 1/2016 |

OTHER PUBLICATIONS

International Search Report dated Jul. 12, 2016 in connection with PCT International Application No. PCT/JP2016/063244.
Product information for 30-3003 Explosion-Proof Smoke Detector, Notifier® by Honeywell, published Mar. 21, 2012.
Product information for 30-3013 Explosion-Proof Smoke Detector, Notifier® by Honeywell, published May 10, 2012.
Aug. 28, 2018 Japanese official action in connection with corresponding Japanese patent application No. 2017-536632.

* cited by examiner

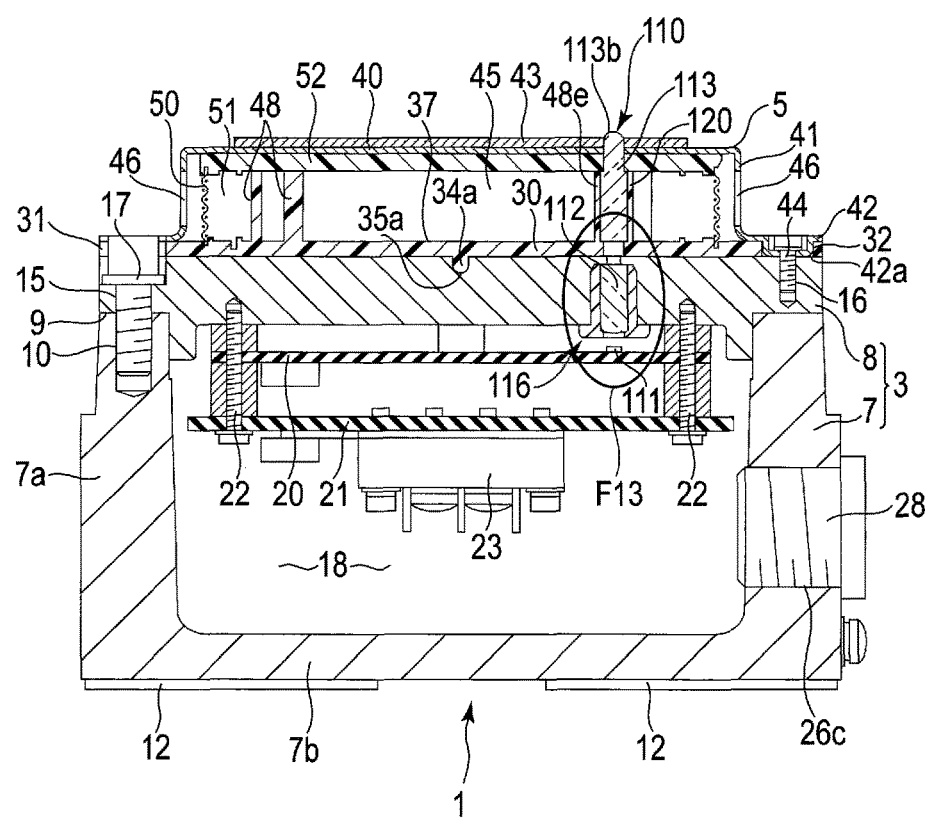
F I G. 5

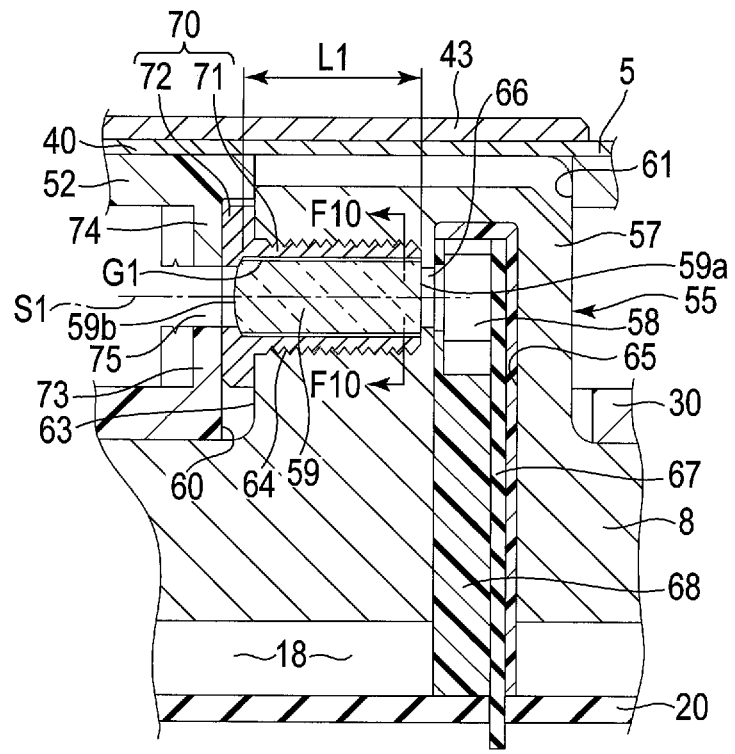
F I G. 9
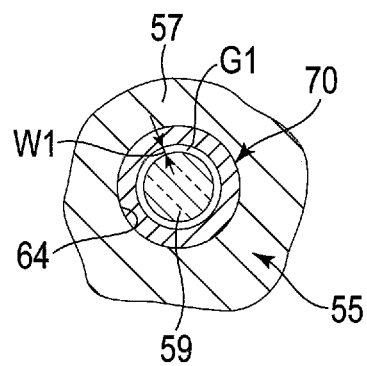
F I G. 10

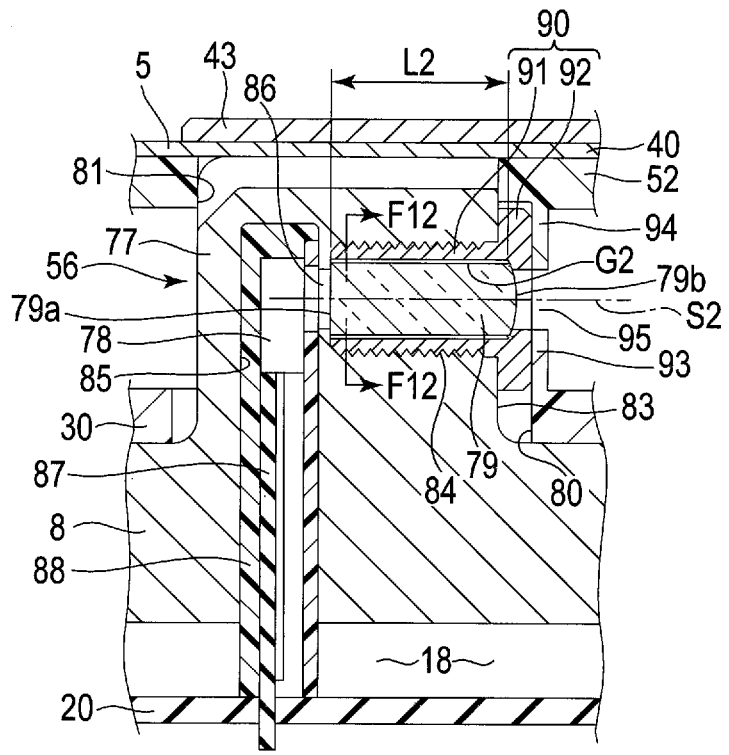
F I G. 11
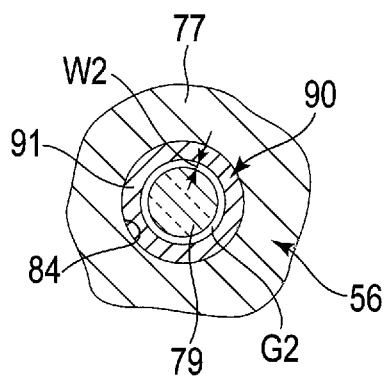
F I G. 12

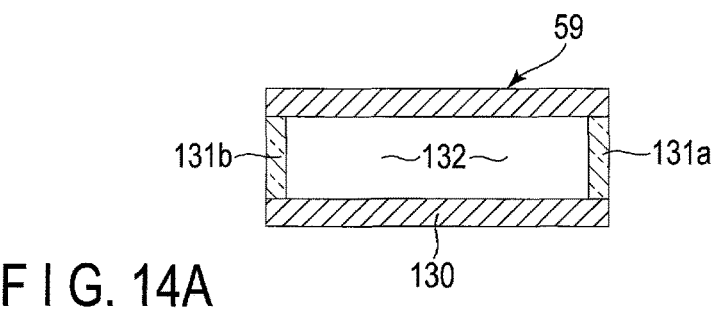
F I G. 14A
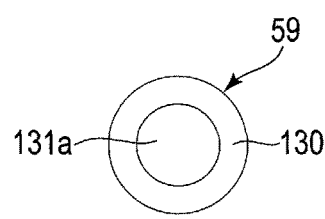
F I G. 14B
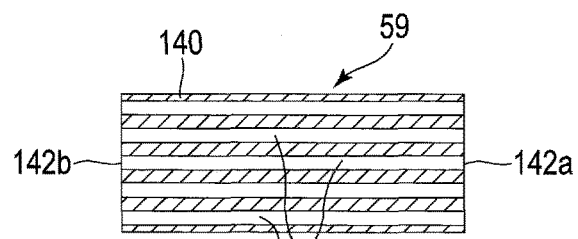
F I G. 15A
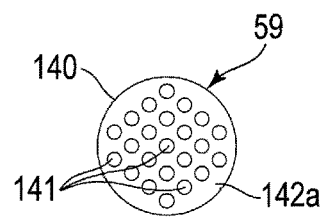
F I G. 15B

PHOTOELECTRIC SMOKE SENSOR

CROSS-REFERENCE TO RELATED APPLICATIONS

This application is a Continuation Application of PCT Application No. PCT/JP2016/063244, filed Apr. 27, 2016 and based upon and claiming the benefit of priority from prior Japanese Patent Application No. 2015-165757, filed Aug. 25, 2015, the entire contents of all of which are incorporated herein by reference.

BACKGROUND OF THE INVENTION

1. Field of the Invention

The present invention relates to a photoelectric smoke sensor installed in a hazardous place including a risk of ignition or explosion and having an explosion-proof structure.

2. Description of the Related Art

Smoke sensors have an advantage of being able to detect the occurrence of fire early. A photoelectric smoke sensor, which is a type of the smoke sensors, comprises a light emitting portion and a light receiving portion in a region where air enters and exits, and the region is shielded from external light by a plurality of shielding walls. When smoke accompanying fire enters, for example, a region inside the sensor, the light radiated from the light emitting portion is irregularly reflected by the smoke, the light receiving portion senses the irregularly reflected light, and the occurrence of fire is thereby detected.

The photoelectric smoke sensor comprises a circuit board electrically connected to the light emitting portion and the light receiving portion. In the circuit board, for example, an electric spark may be generated due to a defect or the like of an electronic component mounted on the circuit board or the temperature of the circuit board may abnormally increase due to deterioration of insulation resistance of the circuit board. If an electric spark or a high-temperature circuit board contacts combustible gas, the combustible gas is ignited and causes explosion.

For this reason, when a photoelectric smoke sensor is installed in a hazardous place having a risk of ignition or explosion, a photoelectric smoke sensor having an explosion-proof structure needs to be adopted.

Patent Literature 1 (JP 3938750 B) discloses a photoelectric smoke sensor employing an explosion-proof structure called an intrinsically safe explosion-proof type. In the intrinsically safe explosion-type photoelectric smoke sensor, the occurrence of an electric spark enough to ignite the combustible gas on the surface of the circuit board is prevented by limiting the magnitude of the current flowing through the circuit board.

Patent Literatures 2 (JP S58-129145 U), 3 (JP S63-008538 A), and 4 (JP S63-020050 U) disclose a photoelectric smoke sensor in which the circuit board is positioned remote from the light emitting portion and the light receiving portion so as not to cause explosion on the surface of the circuit board.

More specifically, the photoelectric smoke sensor of Patent Literature 2 comprises a smoke detecting portion comprising a light emitting element and a light receiving lens, and an electric circuit portion separated from the smoke detecting portion, and the light receiving element of the electric circuit portion is connected to the light receiving lens via an optical fiber.

In the photoelectric smoke sensor of Patent Literature 3, the light emitter, the direct light receiver and the scattered light receiver accommodated in a metal casing are coupled to a dark box into which the smoke flows by first to third optical fibers, and lenses are provided at ends of the first to third optical fibers positioned in the dark box, respectively.

In the photoelectric smoke sensor of Patent Literature 4, a labyrinth base on which smoke flows is separated from a light emitting element and a light receiving element, and the light emitting element and the light receiving element are connected via optical fibers, respectively.

BRIEF SUMMARY OF THE INVENTION

In the photoelectric smoke sensor using the optical fiber, however, the light emitting portion and the light receiving portion for sensing the smoke and the explosion-proof container containing the circuit board are separated from each other, and the photoelectric smoke sensor becoming larger in size cannot be avoided.

Moreover, the optical fiber made of resin has a property of attenuating the optical signal from the light emitting portion to the light receiving portion, and the performance of detecting smoke is deteriorated. Furthermore, optical fibers made of glass are more expensive than the optical fibers formed of resin, which is a problem in terms of costs.

At the same time, in the photoelectric smoke sensor using the optical fiber, a sealant formed of resin needs to be injected into the part where the optical fiber penetrates the explosion-proof container in order to prevent the explosive gas from entering the explosion-proof container containing the circuit board. Since the sealant deteriorates with the lapse of time, the airtightness of the explosion-proof container decreases in accordance with the deterioration of the sealant.

As a result, when the combustible gas leaks to the hazardous place, the combustible gas may enter the explosion-proof container, which is one of factors causing the explosion.

An object of the present invention is to provide a photoelectric smoke sensor in which a flame accompanying an explosion does not leak to a designated explosion-proof zone even if an explosion occurs inside the housing, airtightness of the housing does not need to be ensured by using an exclusive sealant, and an explosion resulting from deterioration of the sealant can be prevented preliminarily.

To achieve this object, a photoelectric smoke sensor according to one of embodiments of the present invention comprises a housing which is installed in a designated explosion-proof zone and has a circuit accommodation chamber to accommodate a circuit board, an inflow chamber which is provided in the housing and communicates with the designated explosion-proof zone, a light emitting portion provided in the inflow chamber, and a light receiving portion provided in the inflow chamber.

The light emitting portion includes a first light guide which guides the light emitted by a light emitting element to the inflow chamber, and a first support portion which surrounds and holds the first light guide and communicates with the circuit accommodation chamber. The light receiving portion includes a second light guide which receives the light emitted by the light emitting element inside the inflow chamber guides the light to a light receiving element, and a second support portion which surrounds and holds the second light guide and communicates with the circuit accommodation chamber.

The first support portion and the second support portion are configured to prevent escape of flame from the circuit accommodation chamber to the inflow chamber.

According to a preferable example of the present invention, the first support portion has a first gap communicating with the circuit accommodation chamber and the inflow chamber between the first support portion and the outer peripheral surface of the first light guide, and the second support portion has a second gap communicating with the circuit accommodation chamber and the inflow chamber between the second support portion and the outer peripheral surface of the second light guide. Each of the sizes of the first and second gaps and the lengths along the depth direction of the first and second gaps is set to a value which prevents escape of the flame from the circuit accommodation chamber to the inflow chamber.

According to a preferable example of the present invention, each of the sizes of the first and second gaps and the lengths of the first and second gaps conforms to an explosion-proof standard.

According to the present invention, even if an explosion occurs in the circuit accommodating chamber inside the housing, the flame generated by the explosion disappears in the process of passing through the first support portion and the second support portion. For this reason, the flame accompanying the explosion can be prevented from leaking into the designated explosion-proof area or igniting combustible or explosive gas in the designated explosion-proof area, and sufficient explosion-proof performance can be obtained.

Furthermore, the tightness of the housing can be ensured sufficiently without using a sealant formed of resin. Therefore, the present invention can contribute to the improvement of the explosion-proof property and maintenance of the photoelectric smoke sensor can be executed easily.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 is a cross-sectional view seen along line F5-F5 of FIG. 4.

FIG. 9 is a cross-sectional view showing a structure of the light emitting portion incorporated in the main body cover.

FIG. 10 is a cross-sectional view seen along line F10-F10 of FIG. 9.

FIG. 11 is a cross-sectional view showing a structure of the light receiving portion incorporated in the main body cover.

FIG. 12 is a cross-sectional view seen along line F12-F12 of FIG. 11.

FIG. 14A is a cross-sectional view showing a first light guide according to Modified Example 1 of the First Embodiment.

FIG. 14B is a front view showing the first light guide according to Modified Example 1 of the First Embodiment.

FIG. 15A is a cross-sectional view showing the first light guide according to Modified Example 2 of the First Embodiment.

FIG. 15B is a front view showing the first light guide according to Modified Example 2 of the First Embodiment.

DETAILED DESCRIPTION OF THE INVENTION

First Embodiment

A First Embodiment of the present invention will be described hereinafter with reference to FIG. 1 to FIG. 13.

Figure 1:
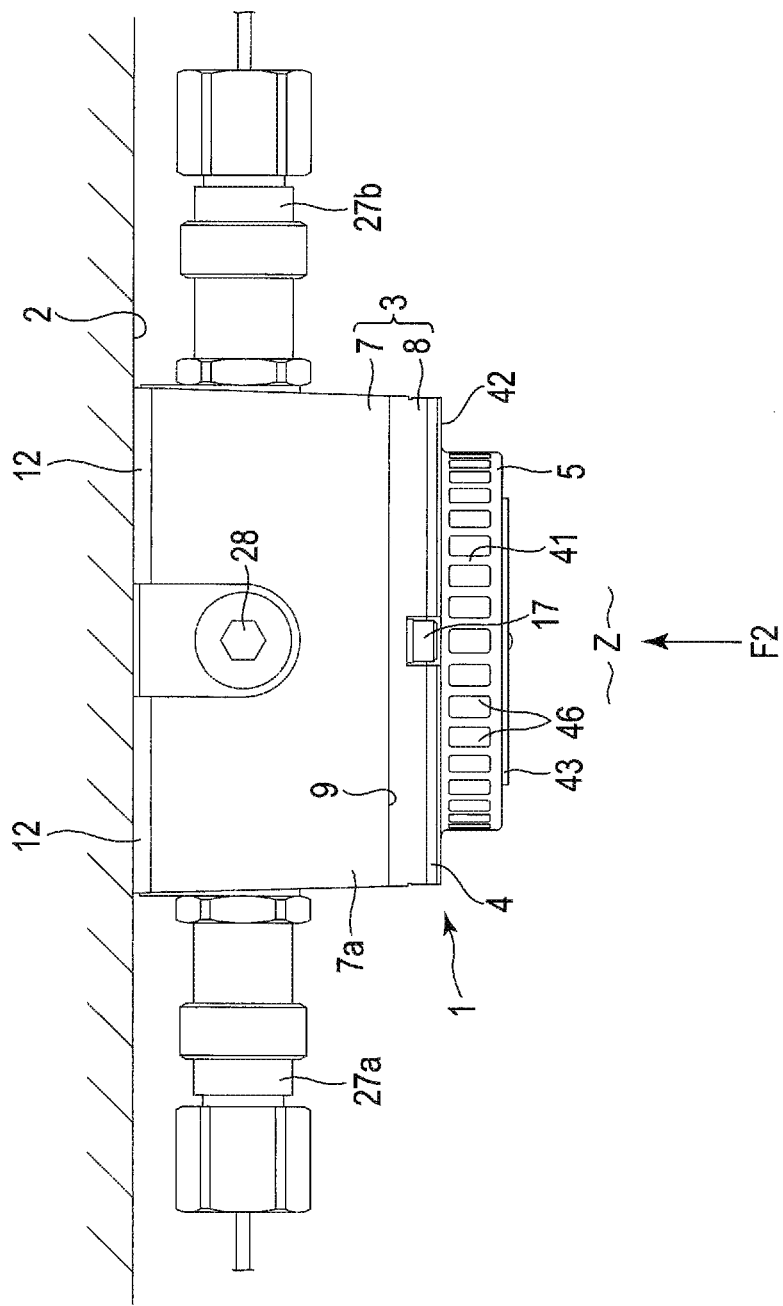
FIG. 1 is a side view showing an integrated photoelectric smoke sensor according to the First Embodiment installed on a ceiling surface of a building.

FIG. 1 shows an integrated photoelectric smoke sensor 1 installed on a ceiling surface 2 of a building. The photoelectric smoke sensor 1 is exposed in a designated explosion-proof area Z in the building. As shown in FIG. 1 to FIG.

3, the photoelectric smoke sensor 1 comprises a housing 3, a chamber base 4, and a protective cover 5 as main elements.

Figure 3:
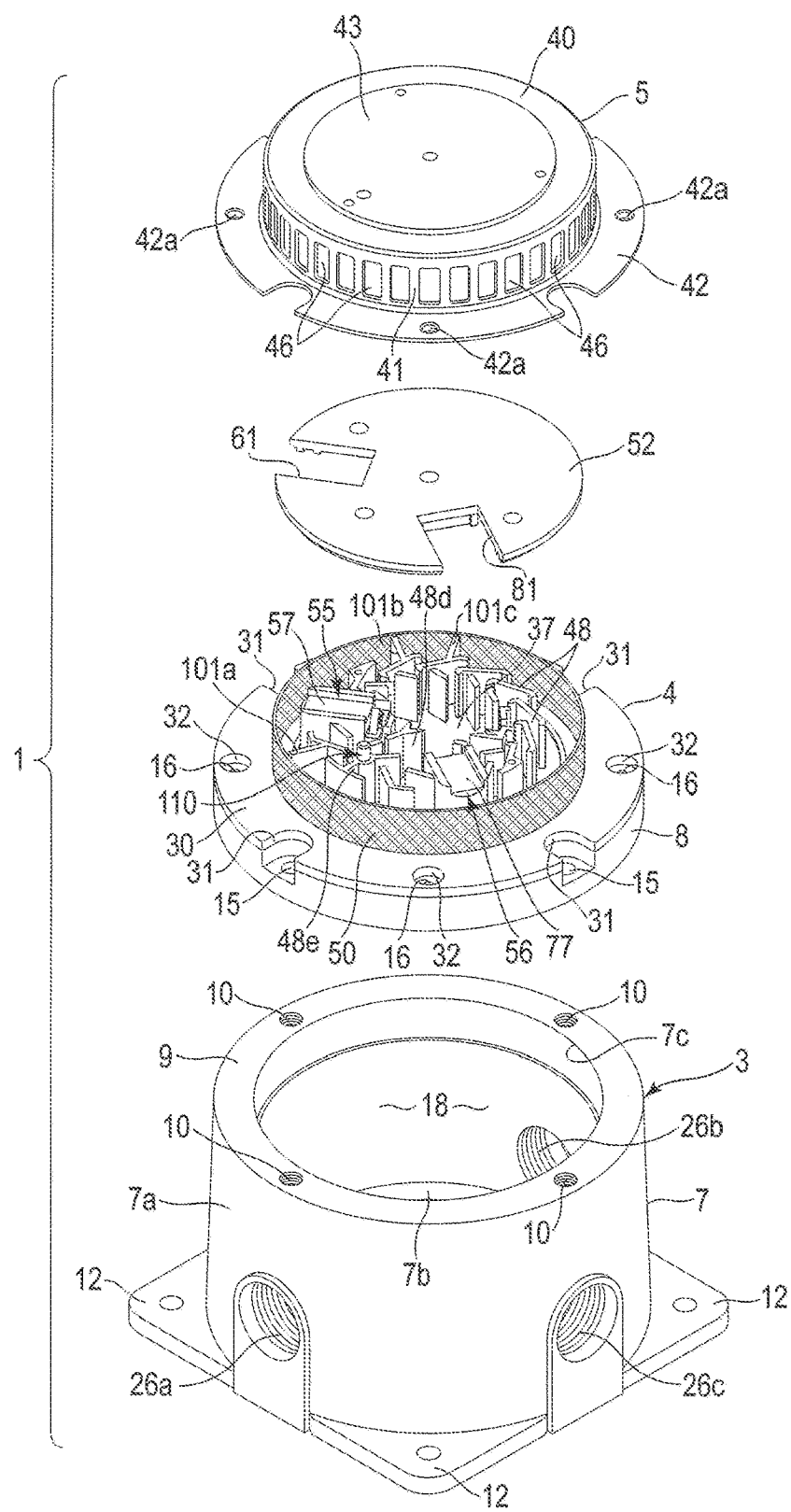
FIG. 3 is an exploded perspective view showing the integrated photoelectric smoke sensor according to the First Embodiment.
Figure 4:
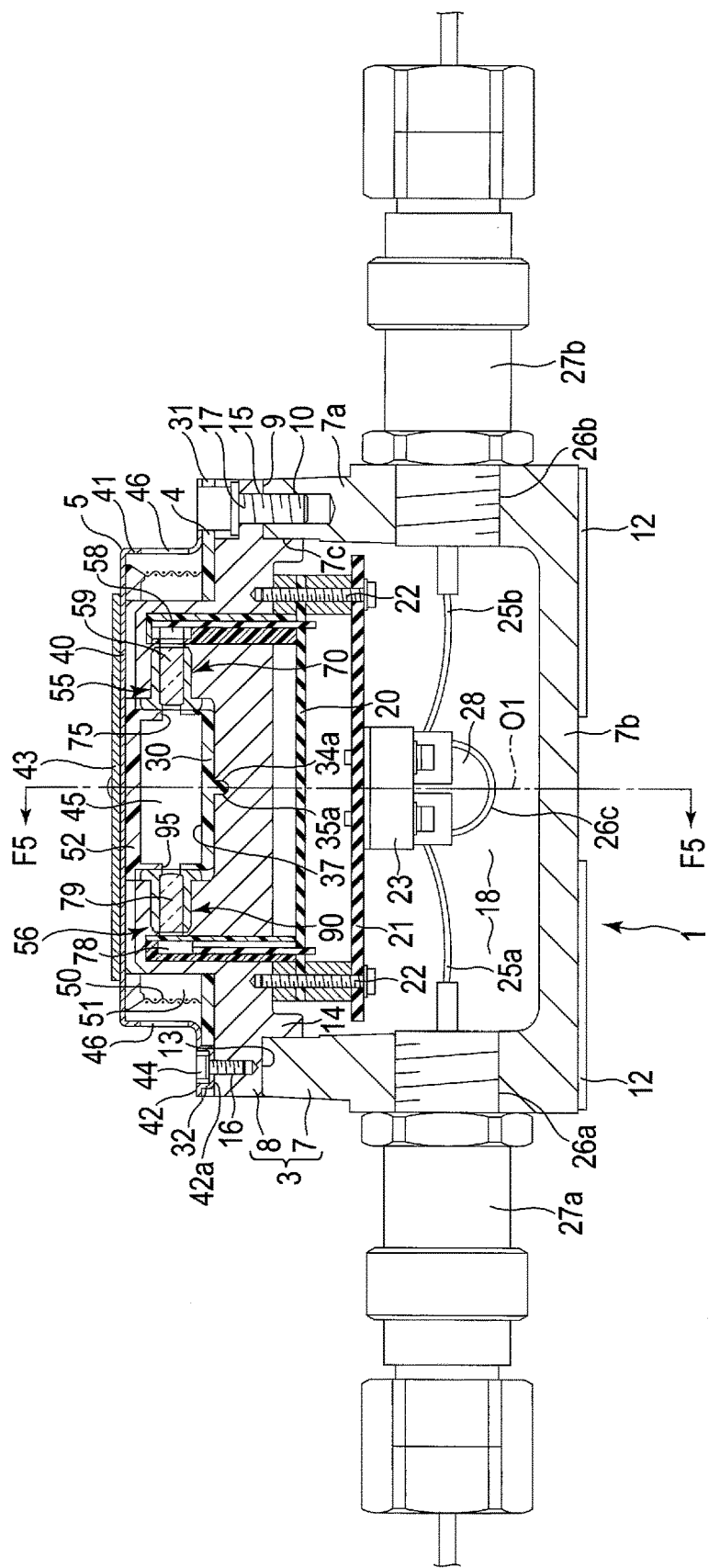
FIG. 4 is a cross-sectional view of the integrated photoelectric smoke sensor according to the First Embodiment.

The housing 3 is formed of, for example, a metal material such as an aluminum alloy. The housing 3 is divided into a main body base 7 and a main body cover 8. As shown in FIG. 3 to FIG. 5, the main body base 7 includes a cylindrical portion 7a and a bottom wall 7b which closes an end of the cylindrical portion 7a. The cylindrical portion 7a has an annular tip surface 9 positioned on a side opposite to the bottom wall 7b. The tip surface 9 is a flat surface orthogonal to axis O1 of the housing 3 passing through the center of the cylindrical portion 7a and defines a circular opening portion 7c at the other end of the cylindrical portion 7a. Four first screw holes 10 are formed on the tip surface 9 of the cylindrical portion 7a. The first screw holes 10 are arranged at intervals in a circumferential direction of the cylindrical portion 7a.

Figure 2:
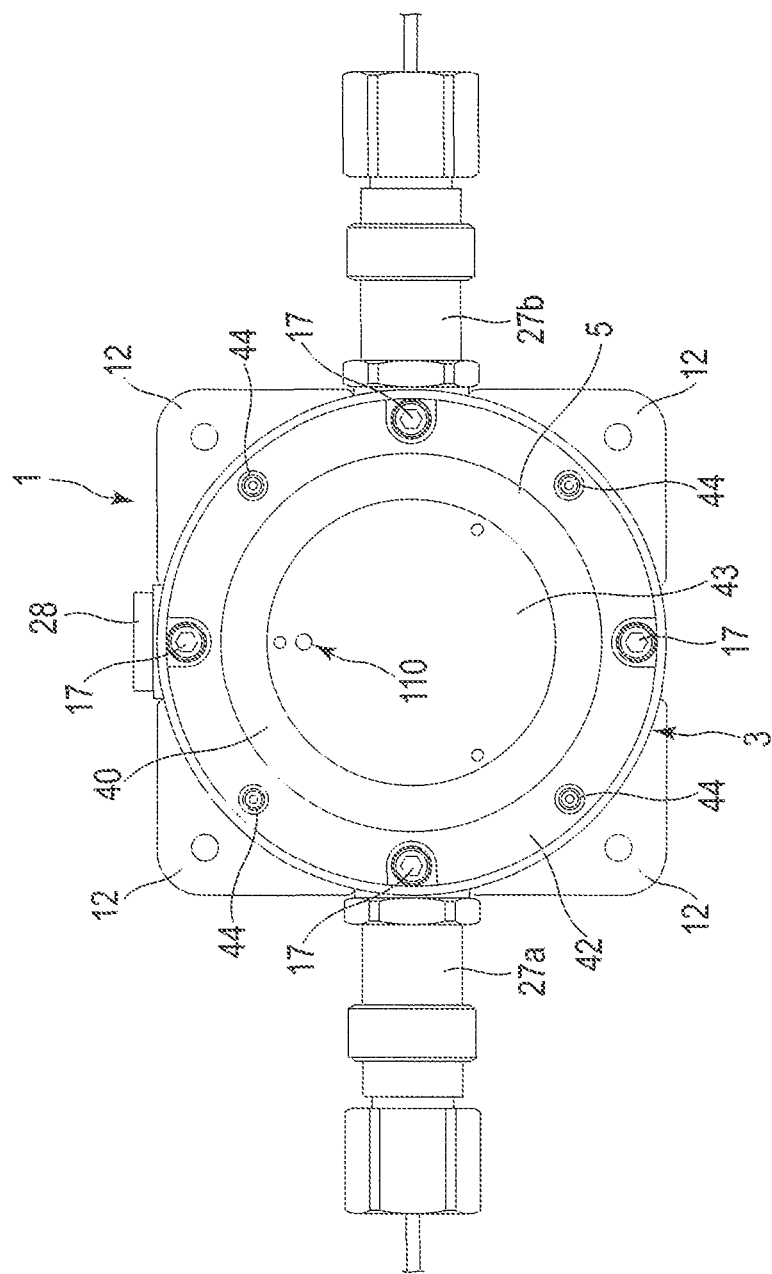
FIG. 2 is a bottom view showing the photoelectric smoke sensor seen from a direction of arrow F2 in FIG. 1.

The bottom wall 7b faces the opening portion 7c. As shown in FIG. 1 and FIG. 2, the bottom wall 7b has a plurality of pedestal portions 12 expanding around the cylindrical portion 7a. The pedestal portions 12 are fixed to the ceiling surface 2 of the building.

The main body cover 8 is a disc-like element having a diameter equivalent to that of the cylindrical portion 7a of the main body base 7. The main body cover 8 has a joint surface 13 overlapping on the tip surface 9 of the cylindrical portion 7a and an annular fitted protruding portion 14 fitted into the opening portion 7c of the cylindrical portion 7a. An outer peripheral surface of the fitted protruding portion 14 is in contact with an inner peripheral surface of the cylindrical portion 7a so as to slide freely.

A plurality of insertion holes 15 and a plurality of second screw holes 16 are formed in an outer peripheral portion of the main body cover 8. The insertion holes 15 are spaced apart from each other in the circumferential direction of the main body cover 8 so as to match the first screw holes 10 of the main body base 7. The second screw holes 16 are spaced apart from each other in the circumferential direction of the main body cover 8 so as to be positioned between the adjacent insertion holes 15.

A plurality of first bolts 17 are screwed into the first screw holes 10 through the insertion holes 15. The main body cover 8 is fixed to the main body base 7 by this screwing. The joint surface 13 of the main body cover 8 is pressed against the tip surface 9 of the main body base 7 and the opening portion 7c of the main body base 7 is closed by the main body cover 8, in a state in which the main body cover 8 is fixed to the main body base 7. As a result, the main body base 7 and the main body cover 8 cooperate with each other to define the circuit accommodation chamber 18 inside the housing 3.

According to the present embodiment, the housing 3 has a pressure-resistant explosion-proof structure in which the housing 3 can withstand the explosion pressure even if the combustible gas explodes in the circuit accommodation chamber 18. More specifically, the housing 3 has a strength so as not to be broken even if, for example, a pressure of approximately 1.5 MPa is applied to the housing due to the explosion in the circuit accommodation chamber 18.

Furthermore, a region from the joint surface 13 of the main body cover 8 to the outer peripheral surface of the fitted protruding portion 14 and a region from the tip surface 9 of the cylindrical portion 7a of the main body base 7 to the inner peripheral surface are in contact with each other and define a sealing portion between the main body cover 8 and the main body base 7, in a state in which the main body cover 8 is fixed to the main body base 7. The size of the gap inevitably generated in the sealing portion and the length of the gap along the thickness direction and the axial direction of the cylindrical portion 7a are set to values conforming to explosion-proof standards, respectively.

The size and length of the gap in the seal portion are varied in accordance with the gas atmosphere of the designated explosion-proof zone Z where the photoelectric smoke sensor 1 is installed, the volume of the circuit accommodation chamber 18, and the like. The size of the gap may be set to, for example, at most 0.3 mm, preferably at most 0.1 mm, and a smaller size of the gap is preferable. The length of the gap in the seal portion may be set to, for example, at least 9.5 mm, preferably at least 40 mm, and a longer gap is preferable.

The escape of the flame traveling through the gap from the circuit accommodation chamber 18 toward the outside of the housing 3 can be prevented by making the size and length of the gap conform to the explosion-proof standards. The flame generated in the circuit accommodation chamber 18 therefore does not leak out of the housing 3.

As shown in FIG. 4 and FIG. 5, a circuit board 20 and a terminal bracket 21 are accommodated in the circuit accommodation chamber 18. The circuit board 20 and the terminal bracket 21 are fixed to the inner surface of the main body cover 8 facing the circuit accommodation chamber 18 with a plurality of screws 22.

A terminal block 23 is supported on a lower surface of the terminal bracket 21. The terminal block 23 is electrically connected to the circuit board 20 via a relay cable (not shown). Furthermore, a pair of cables 25a and 25b are connected to the terminal block 23. The cables 25a and 25b are drawn from the circuit accommodation chamber 18 to the outside of the housing 3 and are electrically connected to, for example, an external device such as an external power supply.

In the present embodiment, cable glands 27a and 27b are screwed into two mounting holes 26a and 26b, respectively, out of three mounting holes 26a, 26b, and 26c opened in the cylindrical portion 7a of the main body base 7. The cables 25a and 25b are drawn from the circuit accommodation chamber 18 to the outside of the housing 3 through the cable glands 27a and 27b.

Furthermore, the remaining one mounting hole 26c is closed with a detachable closing plug 28. The closing plug 28 is screwed into the mounting hole 26c. The direction of drawing the cables 25a and 25b from the housing 3 can be changed by changing connection between the closing plug 28 and the cable gland 27a or 27b.

Gaps allowing screwing of the cable glands 27a and 27b are formed between the mounting holes 26a and 26b and the cable glands 27a and 27b, respectively. Similarly, a gap allowing screwing of the closing plug 28 is formed between the mounting hole 26c and the closing plug 28. The size of these gaps and the length of the gaps along the axial direction of the mounting holes 26a, 26b, and 26c are set to values conforming to the explosion-proof standards.

The escape of the flame traveling through the gap from the circuit accommodation chamber 18 toward the outside of the housing 3 can be prevented by making the size and length of the gap conform to the explosion-proof standards. The flame generated in the circuit accommodation chamber 18 therefore does not leak out of the housing 3.

Figure 6A:
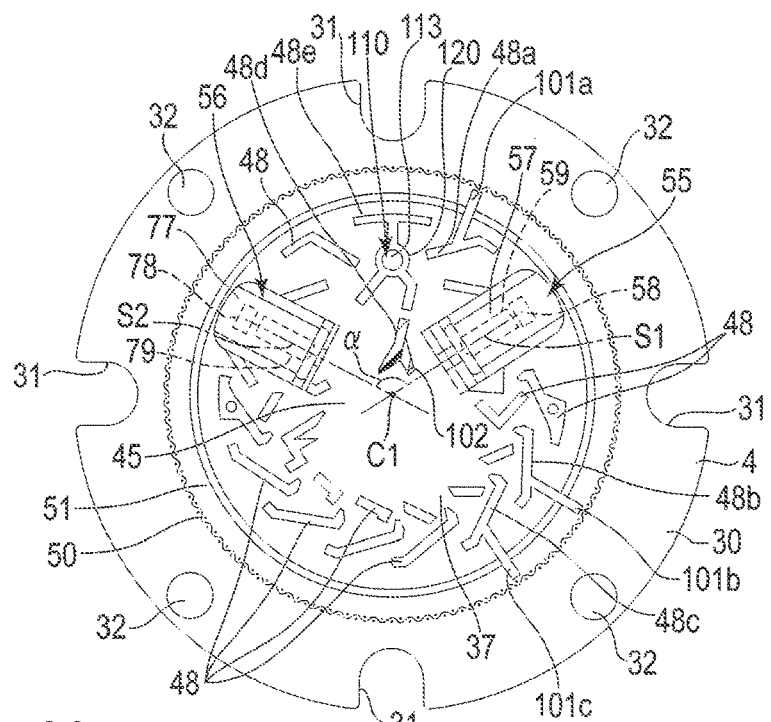
FIG. 6A is a plan view showing a relative positional relationship among a chamber base in which a plurality of shielding walls are formed, a light emitting portion, and a light receiving portion.
Figure 7:
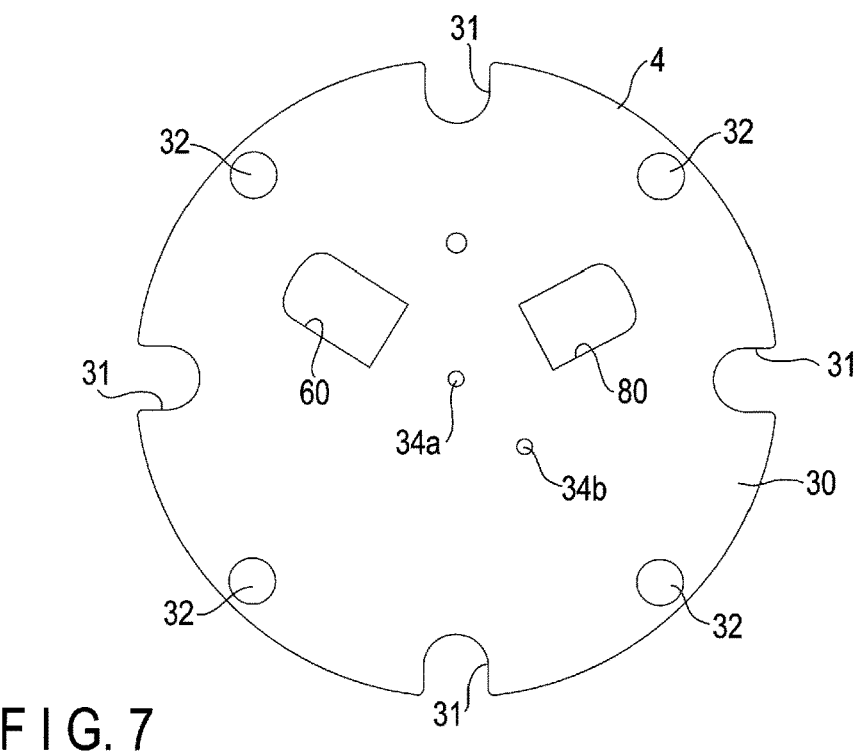
FIG. 7 is a back view showing the chamber base.
Figure 8:
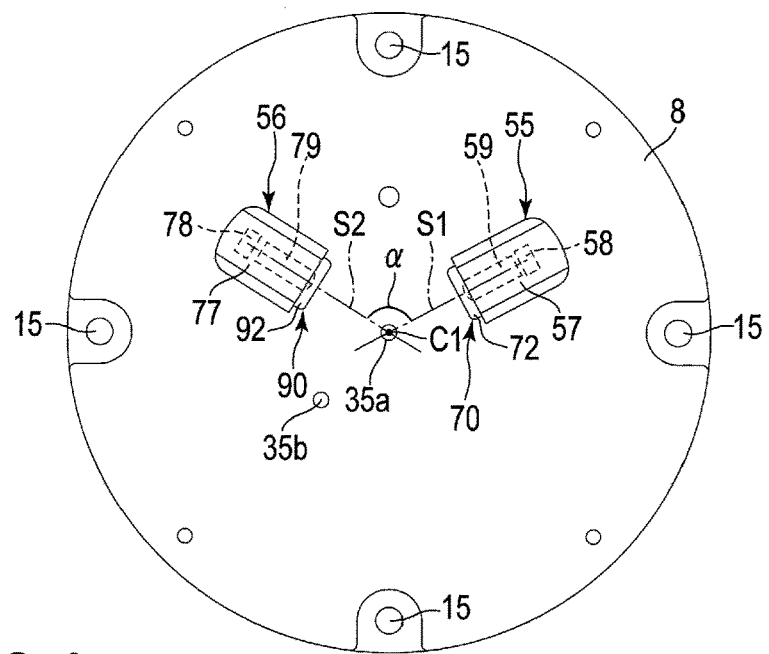
FIG. 8 is a plan view showing a main body cover having a light emitting portion and a light receiving portion.

As shown in FIG. 3 to FIG. 5, the chamber base 4 is superimposed on the main body cover 8. The chamber base 4 is formed of, for example, a resin material such as ABS resin. As shown in FIG. 6A and FIG. 7, the chamber base 4 has a disc-like labyrinth substrate 30 having a diameter equivalent to that of the main body cover 8.

A plurality of notches 31 and a plurality of through holes 32 are formed in the outer peripheral portion of the labyrinth substrate 30. The notches 31 are spaced apart from each other in the circumferential direction of the labyrinth substrate 30 so as to correspond to the insertion holes 15 of the main body cover 8. The through holes 32 are spaced apart from each other in the circumferential direction of the labyrinth substrate 30 so as to match the second screw holes 16 of the main body cover 8 between the adjacent notches 31.

As shown in FIG. 4, FIG. 5, and FIG. 7, a first positioning protrusion 34a and a second positioning protrusion 34b are formed on the back surface of the labyrinth substrate 30. The first positioning protrusion 34a protrudes from the center of the labyrinth substrate 30 toward the surface of the main body cover 8 so as to be located on the axis O1 of the housing 3. The second positioning protrusion 34b protrudes toward the surface of the main body cover 8, at a position eccentric from the center of the labyrinth substrate 30.

A head of the first bolt 17 enters the notch 31 of the labyrinth substrate 30 in a state in which the labyrinth substrate 30 of the chamber base 4 is superposed on the main body cover 8. At the same time, the first positioning protrusion 34a and the second positioning protrusion 34b are fitted into a first recess portion 35a and a second recess portion 35b formed on the surface of the main body cover 8. The first recess portion 35a is located at the center of the main body cover 8 through which the axis O1 of the housing 3 passes. The second recess portion 35b is eccentric from the center of the main body cover 8.

Therefore, the first positioning protrusion 34a is fitted into the first recess portion 35a, the second positioning protrusion 34b is fitted into the second recess portion 35b, and the chamber base 4 is thereby positioned coaxially with the housing 3. At the same time, the chamber base 4 and the main body cover 8 can be prevented from being shifted in the circumferential direction around the axis O1 of the housing 3. Therefore, relative displacement between the housing 3 and the chamber base 4 can be prevented and the position of the chamber base 4 relative to the housing 3 is determined accurately.

As shown in FIG. 3 and FIG. 6A, the labyrinth substrate 30 of the chamber base 4 has a smoke detecting portion 37. The smoke detecting portion 37 is a circular region surrounded by the outer peripheral portion of the labyrinth substrate 30 including the notches 31 and the through holes 32 and is located at the center of the surface of the labyrinth substrate 30. The center of the smoke detecting portion 37 is located above the axis O1 of the housing 3.

The protective cover 5 is put on the chamber base 4 formed of resin. The protective cover 5 is formed of, for example, a steel plate having a thickness of approximately 1 mm. The protective cover 5 has a disk-shaped top portion 40, a cylindrical side plate portion 41 continuous with the outer peripheral edge of the top portion 40, and a ring-shaped flange portion 42 continuous with the front edge of the side plate portion 41.

The top portion 40 faces the smoke detection portion 37 of the chamber base 4. A disk-shaped nameplate 43 is fixed on the top portion 40. The nameplate 43 is formed of, for example, stainless steel having a thickness of approximately 1.5 mm and also has a function of reinforcing the top portion 40. As a result, at least the top portion 40 of the protective cover 5 has the strength conforming to the explosion-proof standard.

The side plate portion 41 surrounds the smoke detecting portion 37 of the chamber base 4. The flange portion 42 protrudes around the side plate portion 41 and is overlapped on the outer peripheral portion of the labyrinth substrate 30.

According to the present embodiment, the flange portion 42 of the protective cover 5 has a plurality of recessed portions 42a that enter the through holes 32 of the labyrinth substrate 30. Bottoms of the recess portions 42a are overlapped on the surface of the main body cover 8.

As shown in FIG. 4 and FIG. 5, a plurality of second fixing bolts 44 pass through the recess portions 42a of the protective cover 5 and are screwed into the second screw holes 16 of the main body cover 8. The protective cover 5 is fixed on the labyrinth substrate 30 and the labyrinth substrate 30 is sandwiched between the flange portion 42 of the protective cover 5 and the surface of the main body cover 8, by this screwing. The labyrinth substrate 30 is therefore fixed to the main body cover 8 via the protective cover 5.

The top portion 40 and the side plate portion 41 of the protective cover 5 cooperate with the smoke sensing portion 37 of the labyrinth substrate 30 to define an inflow chamber 45 on the housing 3, in a state in which the protective cover 5 is fixed on the labyrinth substrate 30. The inflow chamber 45 is located on the side opposite to the circuit accommodation chamber 18 in the housing 3 through the main body cover 8.

Furthermore, a plurality of ventilation ports 46 are formed in the side plate portion 41 of the protective cover 5. The ventilation ports 46 are spaced apart from each other in the circumferential direction of the side plate portion 41 so as to open in the inflow chamber 45. Due to the presence of the ventilation ports 46, the inflow chamber 45 communicates with a designated explosion-proof zone Z of the building, such that the air in the designated explosion-proof zone Z or the air flow including smoke, steam, dust and the like flows into the inflow chamber 45 through the ventilation ports 46.

As shown in FIG. 3, FIG. 5, and FIG. 6A, a plurality of shielding walls 48 are arranged on the outer peripheral portion of the inflow chamber 45. The shielding wall 48 is an element for blocking light entering the inflow chamber 45 from the designated explosion-proof zone Z while permitting the entry and exit of the air and airflow to and from the inflow chamber 45.

The shielding walls 48 are erected integrally from the smoke detecting portion 37 of the labyrinth substrate 30 toward the top portion 40 of the protective cover 5 and are spaced apart from each other in the circumferential direction of the labyrinth substrate 30. For this reason, the shielding walls 48 are located inside the side plate portion 41 of the protective cover 5 and face the ventilation ports 46 of the side plate portion 41.

Furthermore, an insect screen 50 is arranged between the ventilation ports 46 of the protective cover 5 and the shielding walls 48. The insect screen 50 surrounds the smoke detecting portion 37 of the inflow chamber 45 and is distant from the shielding walls 48. For this reason, a ventilation passage 51 is formed between the insect screen 50 and the shielding walls 48 along the circumferential direction of the inflow chamber 45. The ventilation passage 51 communicates with an interval between the adjacent shielding walls 48.

According to the present embodiment, the chamber cover 52 is arranged inside the protective cover 5. The chamber cover 52 is formed of, for example, a resin material such as ABS resin. The chamber cover 52 is overlapped on the back surface of the top portion 40 of the protective cover 5 and is in contact with rising edges of the shielding walls 48. In addition, the insect screen 50 is held between the labyrinth substrate 30 and the chamber cover 52.

As shown in FIG. 3, FIG. 4, and FIG. 6A, a light emitting portion 55 and a light receiving portion 56 are incorporated in the main body cover 8 of the housing 3. Each of the light emitting portion 55 and the light receiving portion 56 can be restated as an optical unit. FIG. 9 is an enlarged view showing the structure of the light emitting portion 55. As shown in FIG. 9, the light emitting portion 55 comprises a first support portion 57, a light emitting diode 58, and a first light guide 59 as main elements.

The first support portion 57 is an element formed integrally with the main body cover 8 and protrudes to the outer peripheral portion of the inflow chamber 45 through a first through hole 60 formed in the labyrinth substrate 30. The protruding end of the first support portion 57 enters a relief portion 61 formed by partially cutting the chamber cover 52. Furthermore, the first support portion 57 is arranged in such a manner of squeezing in a region where the shielding walls 48 are arranged in the outer peripheral portion of the inflow chamber 45.

The first support portion 57 has a tip surface 63, a mounting hole 64, and a hollow portion 65. The tip surface 63 is erected in the inflow chamber 45 so as to face the center C1 of the inflow chamber 45. The center C1 of the inflow chamber 45 is located above the axis O1 of the housing 3. The mounting hole 64 includes one end opened to the tip surface 63 and the other end located inside the first support portion 57. The mounting hole 64 has a straight axis S1 extending horizontally toward the center C1 of the inflow chamber 45.

The hollow portion 65 is erected behind the mounting hole 64. A lower end of the hollow portion 65 penetrates the main body cover 8 and opens into the circuit accommodation chamber 18. An upper end of the hollow portion 65 is positioned inside the first support portion 57 and communicates with the other end of the mounting hole 64 through a communication port 66.

The light emitting diode 58 is an example of a light emitting element and is mounted on one end of an LED substrate 67. The LED substrate 67 is accommodated in the hollow portion 65. The light emitting diode 58 positioned at one end of the LED substrate 67 is positioned above the axis S1 of the mounting hole 64 so as to face the communication port 66. Furthermore, the other end of the LED substrate 67 on the side opposite to the light emitting diode 58 is electrically connected to the circuit board 20 in the circuit accommodation chamber 18.

In the present embodiment, the light emitting diode 58 and the LED substrate 67 are covered with an insulating cover 68 except for the light emitting surface of the light emitting diode 58.

The first light guide 59 is formed of, for example, a columnar colorless and transparent glass. As shown in FIG. 9 and FIG. 10, the first light guide 59 has a flat light receiving surface 59a which faces the light emitting surface of the light emitting diode 58 and a light emitting surface 59b curved in a convex lens shape. The light receiving surface 59a and the light emitting surface 59b are separated from each other in the axial direction of the first light guide 59.

According to the present embodiment, the first light guide 59 is coaxially supported in the mounting hole 64 via a first holder 70. The first holder 70 is formed of a metal material such as an aluminum alloy. The first holder 70 comprises a cylindrical portion 71 in which the first light guide 59 is coaxially fitted and a flange portion 72 formed on one end of the cylindrical portion 71.

The cylindrical portion 71 is screwed into the mounting hole 64 of the first support portion 57 from the direction of the tip surface 63 of the first support portion 57. The first light guide 59 is held inside the first support portion 57, and the flange portion 72 of the first holder 70 abuts on the tip surface 63 of the first support portion 57, by the screwing. The flange portion 72 is fixed to the tip surface 63 with screws (not shown). The first holder 70 is therefore fixed firmly to the first support portion 57.

As shown in FIG. 9, the first light guide 59 is surrounded by the first support portion 57 in a state in which the first light guide 59 is supported by the first support portion 57. Furthermore, the light receiving surface 59a of the first light guide 59 faces the light emitting surface of the light emitting diode 58 through the communication port 66, and the light emitting surface 59b of the first light guide 59 is exposed to the inflow chamber 45.

As shown in FIG. 9 and FIG. 10, a first gap G1 which permits the fitting of the first light guide 59 is provided between the outer peripheral surface of the first light guide 59 and the inner peripheral surface of the cylindrical portion 71 of the first holder 70. The first gap G1 communicates with the inflow chamber 45 and also communicates with the circuit accommodation chamber 18 via the communication port 66 and the hollow portion 65.

If the cylindrical portion 71 and the first light guide 59 maintain the coaxiality, the size W1 of the first gap G1 can be restated as a distance from an arbitrary point on the inner peripheral surface of the cylindrical portion 71 to the outer peripheral surface of the first light guide 59 distant from the first light guide 59 in the radial direction. The length L1 along the depth direction of the first gap G1 is equal to the total length of the first light guide 59 from the outer peripheral edge of the light receiving surface 59a of the first light guide 59 to the outer peripheral edge of the light emitting surface 59b.

Each of the size W1 and the length L1 of the first gap G1 are set to values conforming to the explosion-proof standard. If the size W1 and the length L1 of the first gap G1 conform to the explosion-proof standard, the flame caused by the explosion in the circuit accommodation chamber 18 may reach the first gap G1 through the hollow portion 65 but the escape of the flame moving toward the inflow chamber 45 through the first gap G1 can be prevented.

The size W1 and the length L1 of the first gap G1 are varied according to the gas atmosphere of the designated explosion-proof zone Z where the photoelectric smoke sensor 1 is installed, the volume of the circuit accommodation chamber 18, and the like. The size W1 of the first gap G1 may be set to, for example, at most 0.3 mm, preferably at most 0.1 mm. The smaller size W1 of the first gap G1 is preferable but the size exceeds 0 mm from the viewpoint of manufacturing.

The length L1 of the first gap G1 differs according to the size W1 of the first gap G1. The length L1 of the first gap G1 may be set to, for example, at least 9.5 mm, preferably at least 40 mm, and the longer length L1 of the first gap G1 is desirable.

More specifically, for example, in a case where the designated explosion-proof zone Z is a hydrogen gas atmosphere, the length conforms to the explosion-proof standard if the length L1 of the first gap G1 is at least 9.5 mm when the size W1 of the first gap G1 is 0.1 mm, if the length L1 of the first gap G1 is at least 25.0 mm when the size W1 of the first gap G1 is 0.15 mm, and if the length L1 of the first gap G1 is at least 40.0 mm when the size W1 of the first gap G1 is 0.20 mm.

Furthermore, if the center of the cylindrical portion 71 does not coincide with the center of the first light guide 59 and the size W1 of the first gap G1 is not uniform along the circumferential direction of the first light guide 59, the maximum value of the size W1 of the first gap G1 may be 0.3 mm or less, preferably 0.1 mm or less.

As shown in FIG. 9, the labyrinth substrate 30 has a first protrusion 73 protruding along the tip surface 63 of the first support portion 57. Similarly, the chamber cover 52 has a second protrusion 74 protruding so as to extend along the tip surface 63 of the first support portion 57. A slit 75 which limits the radiation direction of light is formed between the protruding end of the first protrusion 73 and the protruding end of the second protrusion 74. For this reason, the light emitting surface 59b of the first light guide 59 is exposed to the inflow chamber 45 through the slit 75.

Furthermore, in the present embodiment, the first holder 70 is subjected to color anodic oxide coating, and the first holder 70 is entirely covered with a black anodized aluminum film which can easily absorb light. At the same time, the outer peripheral surface of the first light guide 59 facing the inner peripheral surface of the cylindrical portion 71 of the first holder 70 is finished to have a rough surface as a preferable example.

The light receiving portion 56 incorporated in the main body cover 8 basically has the same structure as the light emitting portion 55. FIG. 11 shows the structure of the light receiving portion 56 in an enlarged manner. As shown in FIG. 11, the light receiving portion 56 comprises a second support portion 77, a photodiode 78, and a second light guide 79 as main elements.

The second support portion 77 is an element formed integrally with the main body cover 8 and protrudes to the outer peripheral portion of the inflow chamber 45 through a second through hole 80 formed in the labyrinth substrate 30. A protruding end of the second support portion 77 enters a relief portion 81 formed by partially cutting the chamber cover 52. Furthermore, the second support portion 77 is disposed in such a manner as to be inserted into a region where the shielding walls 48 are arranged in the outer peripheral portion of the inflow chamber 45.

The second support portion 77 has a tip surface 83, a mounting hole 84, and a hollow portion 85. The tip surface 83 is erected in the inflow chamber 45 so as to face the center C1 of the inflow chamber 45. The mounting hole 84 includes one end opened to the tip surface 83 and the other end positioned inside the second support portion 77. The mounting hole 84 has a straight axis S2 extending horizontally toward the center C1 of the inflow chamber 45.

The hollow portion 85 is erected behind the mounting hole 84. A lower end of the hollow portion 85 penetrates the main body cover 8 and opens into the circuit accommodation chamber 18. An upper end of the hollow portion 85 is positioned inside the second support portion 77 and communicates with the other end of the mounting hole 84 through a communication port 86.

The photodiode 78 is an example of a light receiving element and is mounted on one end of a PD substrate 87. The PD substrate 87 is accommodated in the hollow portion 85. The photodiode 78 positioned at one end of the PD substrate 87 is positioned above the axis S2 of the mounting hole 84 so as to face the communication port 86. Furthermore, the other end of the PD substrate 87 on the side opposite to the photodiode 78 is electrically connected to the circuit board 20 in the circuit accommodation chamber 18.

In the present embodiment, the photodiode 78 and the PD substrate 87 are covered with an insulating cover 88 except for the light receiving surface of the photodiode 78.

The second light guide 79 is formed of, for example, a columnar colorless and transparent glass. As shown in FIG. 11 and FIG. 12, the second light guide 79 has a flat light emitting surface 79a opposed to the light receiving surface of the photodiode 78 and a light receiving surface 79b curved in a convex lens shape. The light emitting surface 79a and the light receiving surface 79b are separated from each other in the axial direction of the second light guide 79.

According to the present embodiment, the second light guide 79 is coaxially supported in the mounting hole 84 via the second holder 90. The second holder 90 is formed of, for example, a metal material such as an aluminum alloy. The second holder 90 includes a cylindrical portion 91 in which the second light guide 79 is fitted coaxially, and a flange portion 92 formed at one end of the cylindrical portion 91.

The cylindrical portion 91 is screwed into the mounting hole 84 of the second support portion 77 from the direction of the tip surface 83 of the second support portion 77. The second light guide 79 is held inside the second support portion 77, and the flange portion 92 of the second holder 90 abuts on the tip surface 83 of the second support portion 77, by this screwing. The flange portion 92 is fixed to the tip surface 83 with a screw (not shown). The second holder 90 is therefore fixed firmly to the second support portion 77.

As shown in FIG. 11, the second light guide 79 is surrounded by the second support portion 77 in a state where the second light guide 79 is supported by the second support portion 77. Furthermore, the light emitting surface 79a of the second light guide 79 faces the light receiving surface of the photodiode 78 through the communication port 86, and the light receiving surface 79b of the second light guide 79 is exposed to the inflow chamber 45.

As shown in FIG. 11 and FIG. 12, a second gap G2 which permits the fitting of the second light guide 79 is provided between the outer peripheral surface of the second light guide 79 and the inner peripheral surface of the cylindrical portion 91 of the second holder 90. The second gap G2 communicates with the inflow chamber 45 and also communicates with the circuit accommodation chamber 18 via the communication port 86 and the hollow portion 85.

When the cylindrical portion 91 and the second light guide 79 maintain the coaxiality, the size W2 of the second gap G2 can be restated as a distance from an arbitrary point on the inner peripheral surface of the cylindrical portion 91 to the outer peripheral surface of the second light guide 79 distant from the second light guide 79 in the radial direction. The length L2 along the depth direction of the second gap G2 is equal to the total length of the second light guide 79 from the outer peripheral edge of the light emitting surface 79a of the second light guide 79 to the outer peripheral edge of the light receiving surface 79b.

Each of the size W2 and the length L2 of the second gap G2 are set to values conforming to the explosion-proof standard. If the size W2 and the length L2 of the second gap G2 conform to the explosion-proof standard, the flame caused by the explosion in the circuit accommodation chamber 18 may reach the second gap G2 through the hollow portion 85 but the escape of the flame moving toward the inflow chamber 45 through the second gap G2 can be prevented.

The size W2 and the length L2 of the second gap G2 are varied according to the gas atmosphere of the designated explosion-proof zone Z where the photoelectric smoke sensor 1 is installed, the volume of the circuit accommodation chamber 18, and the like. Since matters relating to the specific size W2 and the length L2 of the second gap G2 are the same as the size W1 and the length L1 of the first gap G1 of the light emitting portion 55, their explanations are omitted.

As shown in FIG. 11, the labyrinth substrate 30 has a third protrusion 93 protruding along the tip surface 83 of the second support portion 77. Similarly, the chamber cover 52 has a fourth protrusion 94 protruding so as to extend along the tip surface 83 of the second support portion 77. A slit 95 which limits the radiation direction of light is formed between the protruding end of the third protrusion 93 and a protruding end of a fourth protrusion 94. For this reason, the light emitting surface 79b of the second light guide 59 is exposed to the inflow chamber 45 through the slit 95.

Furthermore, in the present embodiment, the second holder 90 is subjected to color anodic oxide coating, and the second holder 90 is entirely covered with a black anodized aluminum film which can easily absorb light. At the same time, the outer peripheral surface of the second light guide 79 facing the inner peripheral surface of the cylindrical portion 91 of the second holder 90 is finished to have a rough surface as a preferable example.

As shown most specifically in FIG. 6A, the axis S1 of the mounting hole 64 passing through the center of the first light guide 59 and the axis S2 of the mounting hole 84 passing through the center of the second light guide 79 extend to the center C1 of the inflow chamber 45 and intersect at the center C1 of the inflow chamber 45 at a crossing angle a of 120°. For this reason, the light emitting surface 59b of the first light guide 59 and the light receiving surface 79b of the second light guide 79 are oriented in different directions without facing each other inside the inflow chamber 45.

In addition, as shown in FIG. 6A, first to third guide walls 101a, 101b, and 101c are provided at the outer peripheral portion of the inflow chamber 45 on which the plurality of shielding walls 48 are arranged. The first to third guide walls 101a, 101b, and 101c are erected from the surface of the labyrinth substrate 30, and their respective tips are in contact with the chamber cover 52.

The first guide wall 101a extends toward the outside along the radial direction of the inflow chamber 45 from a shielding wall 48a extending in the peripheral direction of the inflow chamber 45 at a position adjacent to the light emitting portion 55, of the plurality of shielding walls 48 positioned between the light emitting portion 55 and the light receiving portion 56.

The second guide wall 101b and the third guide wall 101c extend toward the outside along the radial direction of the inflow chamber 45 from two shielding walls 48b and 48c extending in the peripheral direction of the inflow chamber 45 on the extension of the axis S2 passing through the center of the second light guide 79, of the plurality of shielding walls 48.

In other words, the first to third guide walls 101a, 101b, and 101c extend radially with respect to the center C1 of the inflow chamber 45. For this reason, the first to third guide walls 101a, 101b, and 101c cross the ventilation passage 51 between the insect screen 50 and the shield wall 48.

Furthermore, as shown in FIG. 6A, one shielding wall 48d located in the vicinity of the center C1 of the inflow chamber 45, of the plurality of shielding walls 48, is positioned on an extension of the first guide wall 101a so as to enter between the tip surface 63 of the first support portion 57 of the light emitting portion 55 and the tip surface 83 of the second support portion 77 of the light receiving portion 56. The shielding wall 48d has a through hole 102 along the radial direction of the inflow chamber 45. The through hole 102 is opened toward the center C1 of the inflow chamber 45.

Figure 13:
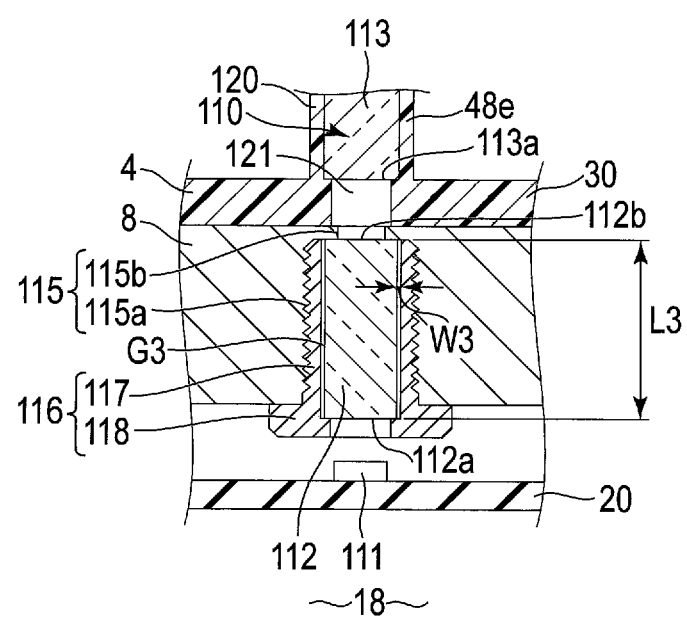
FIG. 13 is an enlarged cross-sectional view showing the portion of F13 of FIG. 5.

As shown in FIG. 5 and FIG. 13, the photoelectric smoke sensor 1 incorporates an indicator lamp 110. The indicator lamp 110 is an element for displaying whether the photoelectric smoke sensor 1 operates normally or not, and is provided at a position eccentric from the center C1 of the inflow chamber 45. The indicator lamp 110 comprises a light emitting diode 111, a first light guide 112 and a second light guide 113 as main elements.

The light emitting diode 111 is mounted on the surface of the circuit board 20. The first light guide 112 is formed of, for example, a columnar colorless and transparent glass. The first light guide 112 has a flat light receiving surface 112a and a flat light emitting surface 112b. The light receiving surface 112a and the light emitting surface 112b are separated from each other in the axial direction of the first light guide 112.

The first light guide 112 is supported by a mounting hole 115 provided in the main body cover 8 via a third holder 116. The mounting hole 115 has a large-diameter portion 115a opened in the circuit accommodation chamber 18 and a small-diameter portion 115b opened toward the labyrinth substrate 30. An open end of the large-diameter portion 115a faces the light emitting diode 111.

The third holder 116 is formed of, for example, a metal material such as an aluminum alloy. The third holder 116 comprises a cylindrical portion 117 in which the first light guide 112 is coaxially fitted and a flange portion 118 formed at one end of the cylindrical portion 117.

The cylindrical portion 117 is screwed into the large-diameter portion 115a of the mounting hole 115 from the side of the circuit accommodation chamber 18. The first light guide 112 is supported by the main body cover 8, and the flange portion 118 of the third holder 116 abuts on the back surface of the main body cover 8, by this screwing. The flange portion 118 is fixed to the back surface of the main body cover 8 with a screw (not shown). The third holder 116 is therefore fixed firmly to the main body cover 8.

As shown in FIG. 13, the light receiving surface 112a of the first light guide 112 faces the light emitting diode 111, and the light emitting surface 112b of the first light guide 112 faces the small-diameter portion 115b of the mounting hole 115, in a state where the first light guide 112 is supported by the main body cover 8.

The second light guide 113 is formed of, for example, a columnar colorless and transparent polycarbonate resin. The second light guide 113 has a flat light receiving surface 113a and a light emitting surface 113b curved in a convex lens shape. The light receiving surface 113a and the light emitting surface 113b are separated from each other in the axial direction of the second light guide 113.

As shown in FIG. 5 and FIG. 6A, the second light guide 113 is fitted into a hollow boss 120 of the shielding wall 48e positioned between the light emitting portion 55 and the light receiving portion 56, and is thereby held by the chamber base 4.

In a state where the second light guide 113 is supported by the chamber base 4, the light receiving surface 113a of the second light guide 113 faces the light emitting surface 112b of the first light guide 112 through a through hole 121 formed in the labyrinth substrate 30 and the small-diameter portion 115b of the mounting hole 115. In other words, the light receiving surface 113a of the second light guide 113 is separated from the light emitting surface 112b of the first light guide 112 by an amount corresponding to the thickness of the labyrinth substrate 30. Furthermore, the tip portion of the second light guide 113 having the light emitting surface 113b penetrates the chamber cover 52, the top portion 40 of the protective cover 5, and the name plate 43 and protrudes into the designated explosion-proof zone Z.

In the indicator lamp 110 of the present embodiment, a third gap G3 which permits the fitting of the first light guide 112 is provided between the outer peripheral surface of the first light guide 112 and the inner peripheral surface of the cylindrical portion 117 of the third holder 116. The third gap G3 communicates with the circuit accommodating chamber 18, and also communicates with the designated explosion-proof zone Z through the small-diameter portion 115b of the mounting hole 115 and a gap formed between the outer peripheral surface of the second light guide 113 and the inner peripheral surface of the boss portion 120.

Size W3 of the third gap G3 can be restated as a distance from an arbitrary point on the inner peripheral surface of the cylindrical portion 117 to the outer peripheral surface of the first light guide 112 separated in the radial direction of the first light guide 112 if the cylindrical portion 117 and the first light guide 112 maintain the coaxiality. Length L3 along the depth direction of the third gap G3 is equal to the total length of the first light guide 112 from the outer peripheral edge of the light receiving surface 112a of the first light guide 112 to the outer peripheral edge of the light emitting surface 112b.

Each of the size W3 and the length L3 of the third gap G3 is set to a value conforming to the explosion-proof standard. If the size W3 and the length L3 of the third gap G3 conform to the explosion-proof standard, the flame caused by the explosion in the circuit accommodation chamber 18 may reach the third gap G3 but the escape of the flame toward the designated explosion-proof zone Z through the gap G3 is hindered.

The size W3 and the length L3 of the third gap G3 are varied according to the gas atmosphere of the designated explosion-proof zone Z where the photoelectric smoke sensor 1 is installed, the volume of the circuit accommodation chamber 18, and the like. The size W3 of the third gap G3 may be set to, for example, at most 0.3 mm, preferably at most 0.1 mm. The smaller size W3 of the third gap G3 is preferable but the size exceeds 0 mm from the viewpoint of manufacturing.

The length L3 of the third gap G3 differs according to the size W3 of the third gap G3. The length L3 of the third gap G3 may be set to, for example, at least 9.5 mm, preferably at least 40 mm, and the longer length L3 of the third gap G3 is preferable.

According to the indicator lamp 110, the light emitted from the light emitting diode 111 is made incident on the light receiving surface 112a of the first light guide 112. The light incident on the light receiving surface 112a passes through the inside of the first light guide 112 in the axial direction and is then radiated from the light emitting surface 112b toward the light receiving surface 113a of the second light guide 113. The light incident on the light receiving surface 113a of the second light guide 113 passes through the inside of the second light guide 113 in the axial direction and is then radiated from the light emitting surface 113b to the designated explosion-proof zone Z.

For this reason, an observer can learn whether the photoelectric smoke sensor 1 operates normally or not by visually observing the light emission state of the light emitting surface 113b of the second light guide 113.

Since the light emitting surface 113b of the second light guide 113 penetrates the nameplate 43 and protrudes into the designated explosion-proof zone Z, the second light guide 113 may be pushed into the protective cover 5 if, for example, some impact is applied to the light emitting surface 113b. In the present embodiment, the path of the light guiding the light emitted from the light emitting diode 111 to the designated explosion-proof zone Z is composed of the first light guide 112 and the second light guide 113, and the light receiving surface 113a of the second light guide 113 is separated from the light emitting surface 112b of the first light guide 112.

For this reason, even if the second light guide 113 is pushed into the protective cover 5, the light receiving surface 113a of the second light guide 113 can be prevented from abutting on the light emitting surface 112b of the first light guide 112. Applying an impact to the glass-made first light guide 112 can be therefore avoided, and the first light guide 112 can hardly be damaged.

In addition, since the impact resistance of the first light guide 112 is secured and the size W3 and the length L3 of the third gap G3 defined between the first light guide 112 and the third holder 116 is not fluctuated undesirably. For this reason, deviation of the third gap G3 from the explosion-proof standard can be avoided, and even if the flame caused by the explosion in the circuit accommodation chamber 18 reaches the third gap G3, the escape of the flame toward the designated explosion-proof zone Z through the third gap G3 can be prevented.

Next, the actions of the photoelectric smoke sensor 1 will be described.

The designated explosion-proof zone Z where the photoelectric smoke sensor 1 is installed indicates, for example, a place where a combustible gas emitted or leaked into the atmosphere and steam of a combustible liquid are mixed with air and a combustible gas having a risk of explosion is generated, and is often called a dangerous place. Since the photoelectric smoke sensor 1 of the present embodiment is a compact integrated type, the smoke sensor is suitable for use in a space which requires the photoelectric smoke sensor 1 to have a small occupation area, for example, a general factory, a gas storage, a chemical warehouse, a chemical factory, and the like.

The photoelectric smoke sensor 1 is not limited to use in a posture in which the pedestal portion 12 of the housing 3 is fixed to the ceiling surface 2 of the building. For example, the pedestal portion 12 of the housing 3 may be installed on the floor surface of the building or may be installed on the side wall surface of the building, and the posture of the photoelectric smoke sensor 1 is not restricted particularly.

As shown in FIG. 1, the photoelectric smoke sensor 1 takes in the air in the designated explosion-proof zone Z from the ventilation ports 46 of the protective cover 5. The air having entered the ventilation ports 46 passes through the insect screen 50 to flow into the ventilation passage 51 and also passes between the adjacent shielding walls 48 to flow into the inflow chamber 45. Since the shielding walls 48 are structures like a labyrinth which allows air to pass but blocks passage of light, external light does not enter the inflow chamber 45.

Since the light emitting portion 55 and the light receiving portion 56 of the photoelectric smoke sensor 1 penetrate through the labyrinth substrate 30 and protrude into the inflow chamber 45, the light emitting portion 55 and the light receiving portion 56 are maintained in a state of being directly exposed to air in the designated explosion-proof zone Z which enters through the ventilation ports 46. That is, the light emitting surface 59b of the first light guide 59 included in the light emitting portion 55 and the light receiving surface 79b of the second light guide 79 included in the light receiving portion 56 can be restated as the tip surfaces exposed to the designated explosion-proof zone Z.

When the photoelectric smoke sensor 1 is in operation, the light emitted from the light emitting diode 58 of the light emitting portion 55 is made incident on the light receiving surface 59a of the first light guide 59. Part of the light incident on the light receiving surface 59a passes through the inside of the first light guide 59 in the axial direction and the remaining light travels toward the light emitting surface 59b while repeating total reflection on the outer peripheral surface of the first light guide 59.

The light reaching the light emitting surface 59b of the first light guide 59 is emitted toward the center C1 of the inflow chamber 45 through the slit 75. The light emitting surface 59b of the first light guide 59 is oriented in a direction different from the light receiving surface 79b of the second light guide 79 in the inflow chamber 45. For this reason, light radiated from the light emitting surface 59b of the first light guide 59 is not made incident on the light receiving surface 79b of the second light guide 79, in a normal state where smoke is not contained in the air flowing into the inflow chamber 45.

When smoke is contained in the air entering the inflow chamber 45 of the photoelectric smoke sensor 1, the light emitted from the light emitting surface 59b of the first light guide 59 to the inflow chamber 45 is irregularly reflected by smoke. Part of the scattered light is thereby made incident on the light receiving surface 79b of the second light guide 79. Part of the light incident on the light receiving surface 79b passes through the inside of the second light guide 79 in the axial direction and the remaining light travels toward the light emitting surface 79a while repeating total reflection on the outer peripheral surface of the second light guide 79.

The light reaching the light emitting surface 79a of the second light guide 79 is emitted toward the photodiode 78, and the photodiode 78 detects the light. As a result, an electric signal indicating that the light has been detected is sent from the photodiode 78 to the circuit board 20 via the PD substrate 87. The circuit board 20 outputs an electric signal to inform the outside that smoke has occurred in the designated explosion-proof zone Z.

More specifically, an electric signal may be sent to an external buzzer to sound a buzzer or the color of light emitted from the light emitting diode 111 on the circuit board 20 may be changed. The light emitted from the light emitting diode 111 is guided to the light emitting surface 113b of the second light guide 113 via the first light guide 112. Since the light emitting surface 113b protrudes to the designated explosion-proof zone Z, the observer can recognize that smoke has occurred in the designated explosion-proof zone Z by visually recognizing that the color of the light emitting surface 113b has changed.

If the combustible gas exists in the designated explosion-proof zone Z, the combustible gas may enter the circuit accommodation chamber 18 in the housing 3 through, for example, the gap inevitably generated at the sealing portion between the main body base 7 and the main body cover 8, the gap between the mounting holes 26a and 26b of the housing 3 and the cable glands 27a and 27b, the gap between the mounting hole 26c of the housing 3 and the closing plug 28, the first gap G1 between the outer peripheral surface of the first light guide 59 and the inner peripheral surface of the cylindrical portion 71 of the first holder 70, the second gap G2 between the outer peripheral surface of the second light guide 79 and the inner peripheral surface of the cylindrical portion 91 of the second holder 90, and the third gap G3 between the outer peripheral surface of the first light guide 112 and the cylindrical portion 117 of the third holder 116.

The combustible gas which has entered the circuit accommodation chamber 18 may cause an explosion, for example, when a spark resulting from a short current generated on the surface of the circuit board 20 or an abnormal high temperature part occurs on the surface of the circuit board 20.

According to the present embodiment, the housing 3 defining the circuit accommodation chamber 18 can sufficiently withstand the explosion in the circuit accommodation chamber 18 without being damaged since the housing has a pressure-resistant explosion-proof structure. More specifically, the housing 3 is formed of a metal material such as an aluminum alloy having a predetermined thickness so as not to be damaged even if, for example, a pressure of approximately 1.5 MPa defined by the explosion-proof standard is applied.

The flame generated by the explosion in the circuit accommodation chamber 18 is therefore confined inside the housing 3 and does not leak out to the designated explosion-proof zone Z via the inflow chamber 45.

In contrast, the flame generated by the explosion in the circuit accommodation chamber 18 rises in the direction of the inflow chamber 45 along the clearance between the hollow portion 65 of the light emitting portion 55 and the insulating cover 68, and reaches the first gap G1 between the first light guide 59 and the first holder 70 through the communication port 66.

Similarly, the flame in the circuit accommodation chamber 18 rises in the direction of the inflow chamber 45 along the clearance between the hollow portion 85 of the light receiving portion 56 and the insulating cover 88, and reaches the second gap G2 between the second light guide 79 and the second holder 90 through the communication port 86. Furthermore, the flame in the circuit accommodation chamber 18 reaches the third gap G3 between the first light guide 112 and the third holder 116 constituting the indicator lamp 110.

The flame which has reached the first gap G1 travels toward the light emitting surface 59b of the first light guide 59 along the first gap G1. The flame which has reached the second gap G2 travels toward the light receiving surface 79b of the second light guide 79 through the second gap G2. Furthermore, the flame which has reached the third gap G3 travels toward the second light guide 113 along the third gap G3.

According to the present embodiment, the size W1 and the length L1 of the first gap G1, the size W2 and the length L2 of the second gap G2, the size W3 and the length L3 of the third gap G3 are set to values conforming to the explosion-proof standard, respectively. For this reason, the flames which have reached the first to third gaps G1, G2, and G3 naturally disappear in the course of traveling through the first to third gaps G1, G2, and G3, and the flames are not ejected from the first to third gaps G1, G2, and G3 toward the inflow chamber 45.

Thus, the flame generated in the circuit accommodation chamber 18 does not ignite combustible gas entering the inflow chamber 45 from the ventilation port 46 of the protective cover 5, and the explosion accident in the designated explosion-proof zone Z can be prevented preliminarily.

More specifically, if the photoelectric smoke sensor 1 according to the present embodiment is installed in a first class hazardous place where an explosive atmosphere may be frequently produced in a normal state, the flame generated in the circuit accommodation chamber 18 does not ignite the explosive gas outside the housing 3 although the first to third gaps G1, G2, and G3 of the photoelectric smoke sensor 1 communicate with the first class hazardous place via the inflow chamber 45.

According to the present embodiment, the light emitting portion 55 of the photoelectric smoke sensor 1 may be formed such that the size W1 and the length L1 of the first gap G1 conform to the explosion-proof standard. Similarly, the light receiving portion 56 may be formed such that the size W2 and the length L2 of the second gap G2 conform to the explosion-proof standard. Furthermore, the size W3 and the length L3 of the third gap G3 may be formed so as to conform to the explosion-proof standard even at the indicator lamp 110, too. For this reason, a troublesome and burdensome operation of filling each of the first to third gaps G1, G2, and G3 with a sealant formed of a resin is unnecessary, and the photoelectric smoke sensor 1 can easily be manufactured.

In addition, since the first to third gaps G1, G2, and G3 do not need to be filled with the sealing material, inconvenience that the flame generated in the circuit accommodation chamber 18 through the cracks and holes due to aged deterioration of the sealing material may leak out into the inflow chamber 45 can be solved. The flame generated in the circuit accommodation chamber 18 therefore does not ignite the explosive gas outside the housing 3.

According to the photoelectric smoke sensor 1 of the present embodiment, as shown in FIG. 6A, the first to third guide walls 101a, 101b, and 101c are provided in the ventilation passage 51 between the plurality of shielding walls 48 and the insect screen 50. The first guide wall 101a extends in the radial direction of the inflow chamber 45 from one shielding wall 48a at a position adjacent to the first support portion 57 of the light emitting portion 55. The second guide wall 101b and the third guide wall 101c extend in the radial direction of the inflow chamber 45 on the side opposite to the second support portion 77 of the light receiving portion 56 across the center C1 of the inflow chamber 45. The second guide wall 101b is separated from the first guide wall 101a in the circumferential direction of the inflow chamber 45. Furthermore, the second guide wall 101b and the third guide wall 101c are arranged at intervals in the circumferential direction of the inflow chamber 45.

The first to third guide walls 101a, 101b, and 101c therefore extend radially with respect to the center C1 of the inflow chamber 45 around the light emitting portion 55 which is inserted between the plurality of shielding walls 48.

The presence of the first to third guide walls 101a, 101b, and 101c facilitates the air containing smoke which has passed through the ventilation ports 46 of the protective cover 5 and the insect screen 50 to flow into the center C1 of the inflow chamber 45, and whether the smoke is contained in the air or not can be detected optically and accurately.

The reason for this will be explained with respect to FIG. 6B. In the photoelectric smoke sensor 1, making the air containing smoke flow from the entire circumference of the inflow chamber 45 toward the center C1 of the inflow chamber 45 is important to accurately detect the presence of the smoke since the light emitted from the light emitting portion 55 passes through the center C1 of the inflow chamber 45.

According to the photoelectric smoke sensor 1 of the present embodiment, the light emitting portion 55 and the light receiving portion 56 are disposed to be arranged in a region where the plurality of shielding walls 48 are arranged, and the first support portion 57 of the light emitting portion 55 and the second supporting portion 77 of the light receiving portion 56 have a larger shape than the individual shielding walls 48. For this reason, the inventor engaged in the development of the photoelectric smoke sensor 1 has found that the first support portion 57 and the second support portion 77 serve as walls preventing the flow of air from the ventilation passage 51 toward the center C1 of the inflow chamber 45 and that air can thereby hardly flow into the center C1 of the inflow chamber 45.

Figure 6B:
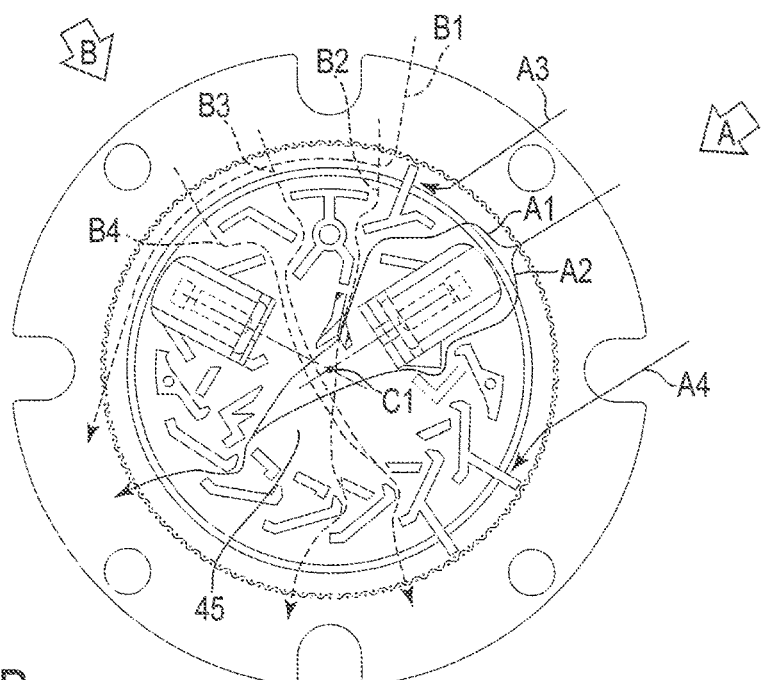
FIG. 6B is a plan view showing an inflow chamber indicating a flow path of air containing smoke.

The inventor conducted a test to examine in which path smoke actually flows through the inflow chamber 45 when the direction of smoke flowing from the outside of the insect screen 50 toward the light emitting portion 55 is represented by A and the direction of smoke flowing from the outside of the insect screen 50 toward the region between the light emitting portion 55 and the light receiving portion 56 is represented by B as shown in FIG. 6B.

Smoke flowing toward the region between the first guide wall 101a and the second guide wall 101b, of the smoke flowing from the direction A to the inflow chamber 45 in FIG. 6B is branched to two flows A1 and A2 by the first support portion 57 of the light emitting portion 55. One of the smoke flows A1 passes between the shielding wall 48a having the first guide wall 101a and one side surface of the first support portion 57 and heads toward the center C1 of the inflow chamber 45. The other smoke flow A2 passes between the shielding wall 48 and the other side surface of the first support portion 57 and heads toward the center C1 of the inflow chamber 45. As a result, two branched smoke flows A1 and A2 join in the vicinity of the center C1 of the inflow chamber 45.

Furthermore, part of the smoke flowing into the region between the first guide wall 101a and the second guide wall 101b from the direction A in FIG. 6B becomes two flows A3 and A4 along the circumferential direction of the inflow chamber 45 and flows through the ventilation passage 51. The flow A3 is blocked by the first guide wall 101a. The flow A4 is blocked by the second guide wall 101b and the third guide wall 101c.

As a result, the flow velocity of the smoke flowing along the circumferential direction of the inflow chamber 45 decreases, and the smoke can easily flow from the vicinity of the light emitting portion 55 toward the center C1 of the inflow chamber 45, in the region between the first guide wall 101a and the second guide wall 101b.

In contrast, the flow B1 of the smoke heading toward the light emitting portion 55 in the ventilation passage 51, of the smoke flowing from the direction B toward the inflow chamber 45 in FIG. 6B, is blocked by the first guide wall 101a and most of the smoke flows toward the second support portion 77 of the light receiving portion 56. That is, smoke heading from the direction B toward the inflow chamber 45 can hardly be diffused in the direction of the light emitting portion 55 and flows in the ventilation passage 51 in a direction of flowing away from the first guide wall 101a, due to the presence of the first guide wall 101a. As a result, the flow velocity of the smoke flowing through the ventilation passage 51 decreases.

Furthermore, the smoke in the ventilation passage 51 heads to the center C1 of the inflow chamber 45 as a plurality of flows B2, B3, and B4 passing between the plurality of adjacent shield walls 48. The plurality of smoke flows B2, B3, and B4 join in the vicinity of the center C1 of the inflow chamber 45.

As a result, the smoke flows A1, A2, B2, B3, and B4 join together in the vicinity of the center C1 of the inflow chamber 45 and the smoke density accordingly increases in the vicinity of the center C1 of the inflow chamber 45.

In addition, according to the present embodiment, the shielding wall 48d located on the extension of the first guide wall 101a in the vicinity of the center C1 of the inflow chamber 45 has the through hole 102 opened toward the center C1 of the inflow chamber 45. For this reason, the smoke flows A1 and B2 head toward the center C1 of the inflow chamber 45 through the through hole 102 without being blocked by the shielding wall 48d as shown in FIG. 6B.

Therefore, according to the photoelectric smoke sensor 1 of the present embodiment, the air flow can be controlled such that air containing the smoke flows passes in the vicinity of the center C1 of the inflow chamber 45, by providing the first to third guide walls 101a, 101b, and 101c. Moreover, since the concentration of smoke is increased in the vicinity of the center C1 of the inflow chamber 45, the ability to detect the smoke can be maximized and the time required for smoke detection can be reduced.

According to the photoelectric smoke sensor 1 of the present embodiment, the first light guide 59 for guiding the light emitted from the light emitting diode 58 to the inflow chamber 45 is fitted in the cylindrical portion 71 of the first holder 70, and the cylindrical portion 71 is screwed into the mounting hole 64 of the first support portion 57 and thereby held in the first support portion 57. The first holder 70 is an element different from the first support portion 57 integrated with the main body cover 8. For this reason, the first holder 70 can be precisely machined into a desired shape and dimensions by using, for example, a machine tool such as a lathe in a state of a single piece before being incorporated in the first support portion 57.

Similarly, the second light guide 79 for receiving the light irregularly reflected by smoke is fitted in the cylindrical portion 91 of the second holder 90, and the cylindrical portion 91 is screwed into the mounting hole 84 of the second support portion 77 and thereby held in the second support portion 77. The second holder 90 is an element different from the second support portion 77 integrated with the main body cover 8. For this reason, the second holder 90 can be precisely processed into a desired shape and dimension by using, for example, a machine tool such as a lathe in a state of a single piece before being incorporated in the second support portion 77.

As a result, the dimensional accuracy of the first holder 70 and the second holder 90 can be increased, and variations in dimensions can also be reduced. The size W1 and the length L1 of the first gap G1 generated between the first light guide 59 and the cylindrical portion 71 of the first holder 70 can be therefore set with high accuracy. Similarly, the size W2 and the length L2 of the second gap G2 generated between the second light guide 79 and the cylindrical portion 91 of the second holder 90 can be set with high accuracy.

As a result, even if the flame generated in the circuit accommodation chamber 18 reaches the first gap G1 and the second gap G2, the escape of the flame from the first gap G1 and the second gap G2 toward the inflow chamber 45 can be certainly prevented and the explosion-proof property of the photoelectric smoke sensor 1 can be enhanced.

In addition, in the present embodiment, the first holder 70 and the second holder 90 are entirely covered with a black anodized aluminum film which can easily absorb light, and the outer peripheral surface of the first light guide 59 and the outer peripheral surface of the second light guide 79 are finished as rough surfaces.

According to this configuration, the light emitted from the outer peripheral surface of the first light guide 59 and the outer peripheral surface of the second light guide 79 can be absorbed by the first holder 70 and the second holder 90, and the Irregular reflection of light can be suppressed on the outer peripheral surface of the first light guide 59 and the outer peripheral surface of the second light guide 79.

As a result, the light emitted from the light emitting diode 58 can be efficiently guided to the inflow chamber 45 from the light emitting surface 59b of the first light guide 59. Furthermore, the light received by the light receiving surface 79b of the second light guide 79 can be certainly guided to the photodiode 78. The reliability in optically detecting whether smoke is contained in the air flowing into the inflow chamber 45 or not is therefore improved.

According to the present embodiment, the labyrinth substrate 30 having the shielding walls 48 is detachably fixed to the main body cover 8 via the second fixing bolts 44. For this reason, when maintenance of the light emitting portion 55 or the light receiving portion 56 protruding from the main body cover 8 is executed, the periphery of the light emitting portion 55 and the light receiving portion 56 can be widely opened merely by canceling the fixing of the labyrinth substrate 30 with the second fixing bolts 44 and detaching the labyrinth substrate 30 from the top portion of the main body cover 8 together with the labyrinth substrate 30. The operations required for the maintenance of the light emitting portion 55 and the light receiving portion 56 can easily be therefore executed.

Furthermore, in the present embodiment, the first positioning protrusion 34a and the second positioning protrusion 34b of the chamber base 4 are fitted in the first recess portion 35a and the second recess portion 35b of the main body cover 8, respectively. Even if an explosion occurs in the circuit accommodation chamber 18 in the housing 3, the chamber base 4 and the housing 3 can be prevented from being displaced in the circumferential direction due to the impact, by adopting this configuration.

The configuration of the first light guide 59 guiding the light of the light emitting diode 58 to the inflow chamber 45 is not particularly limited to the First Embodiment but can be modified in various forms for implementation.

FIG. 14A and FIG. 14B disclose Modified Example 1 of the first light guide 59. The first light guide 59 according to Modification Example 1 is composed of a metallic cylindrical body 130, a transparent first glass plate 131a closing one open end of the body 130, and a transparent second glass plate 131b closing the other open end of the body 130. The space inside the body 130 functions as a passage 132 through which light passes.

FIG. 15A and FIG. 15B disclose Modified Example 2 of the first light guide 59. The first light guide 59 according to Modified Example 2 is composed of a metallic columnar body 140 and a plurality of through holes 141 penetrating the body 140 in the axial direction. The body 140 has a flat first end surface 142a and a flat second end surface 142b. The first end surface 142a and the second end surface 142b are separated from each other in the axial direction of the body 140. Through holes 141 are arranged in the main body 140 at intervals and are opened to the first end surface 142a and the second end surface 142b.

Figure 16A:
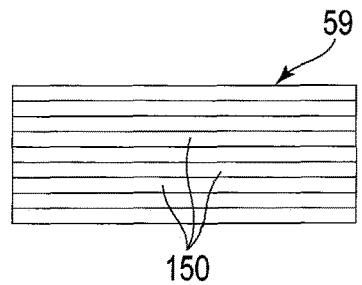
FIG. 16A is a side view showing the first light guide according to Modified Example 3 of the First Embodiment.
Figure 16B:
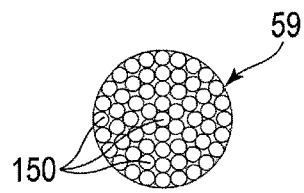
FIG. 16B is a front view showing the first light guide according to Modified Example 3 of the First Embodiment.

FIG. 16A and FIG. 16B disclose Modified Example 3 of the first light guide 59. The first light guide 59 according to Modified Example 3 is configured by bundling a plurality of glass optical fibers 150 in a columnar shape.

Figure 17A:
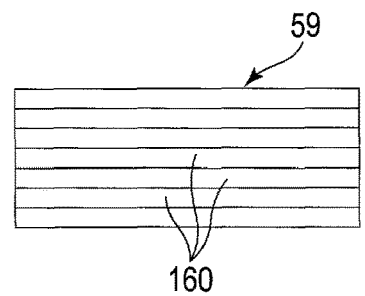
FIG. 17A is a side view showing the first light guide according to Modified Example 4 of the First Embodiment.
Figure 17B:
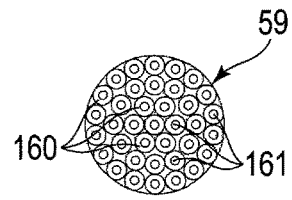
FIG. 17B is a front view showing the first light guide according to Modified Example 4 of the First Embodiment.

FIG. 17A and FIG. 17B disclose Modified Example 4 of the first light guide 59. The first light guide 59 according to Modified Example 4 is configured by bundling a plurality of glass tubes 160 in a columnar shape. Each of the glass tubes 160 has, for example, a hole 161 having an inner diameter of approximately 0.1 mm.

Figure 18A:
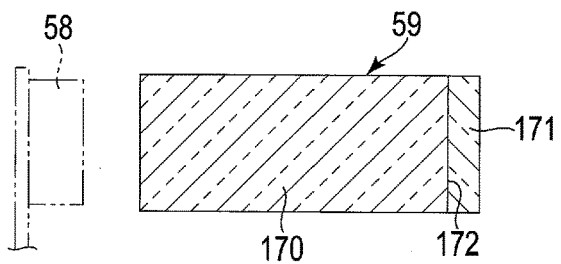
FIG. 18A is a cross-sectional view showing the first light guide according to Modified Example 5 of the First Embodiment.
Figure 18B:
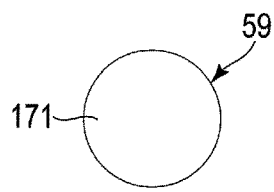
FIG. 18B is a front view showing the first light guide according to Modified Example 5 of the First Embodiment.

FIG. 18A and FIG. 18B disclose Modified Example 5 of the first light guide 59. The first light guide 59 according to Modification Example 5 is composed of a columnar glass body 170 and a disk-like polarizing plate 171. The body 170 has a flat end surface 172 positioned on a side opposite to the light emitting diode 58, and the polarizing plate 171 is stacked on the end surface 172.

Second Embodiment

Figure 19:
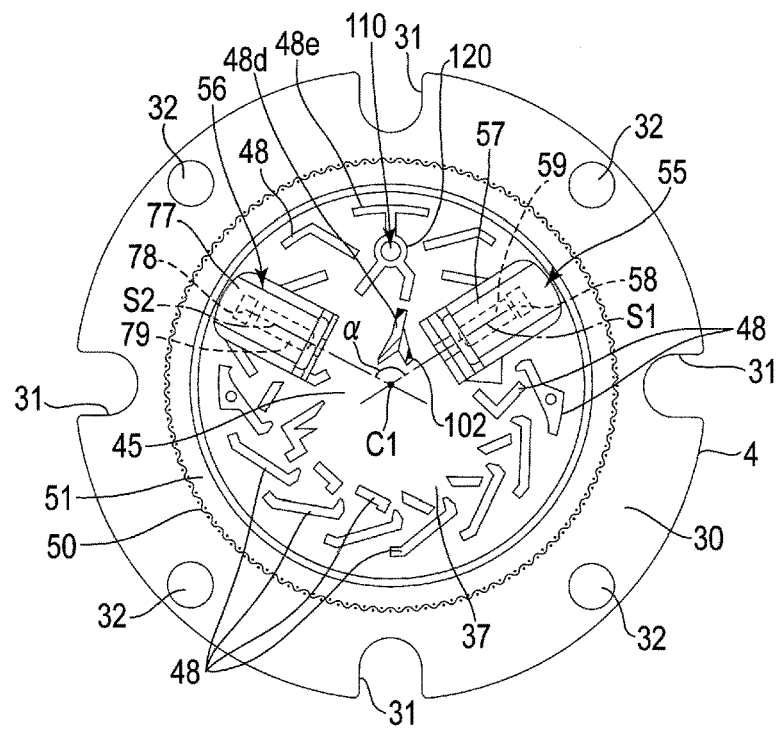
FIG. 19 is a plan view showing the relative positional relationship among a labyrinth substrate on which a plurality of shielding walls are formed, a light emitting portion, and a light receiving portion, in a Second Embodiment.

FIG. 19 discloses a Second Embodiment. In the Second Embodiment, elements corresponding to the first to third guide walls 101a, 101b, and 101c of the First Embodiment are excluded from an outer peripheral portion of a labyrinth substrate 30. The basic configuration of the photoelectric smoke sensor 1 other than those is the same as that of the First Embodiment. For this reason, in the Second Embodiment, the same constituent portions as those in the First Embodiment are denoted by the same reference numerals and their explanations are omitted.

According to the Second Embodiment, a ventilation passage 51 positioned between a plurality of shielding walls 48 and an insect screen 50 maintains an annular shape continuous in a circumferential direction of a ventilation chamber 45. In other words, since the annular insect screen 50 is distant from the shielding walls 48, air flowing from the ventilation ports 46 of the protective cover 5 can easily pass through the insect screen 50.

At the same time, since the air having passed through the insect screen 50 can move freely in the circumferential direction of the inflow chamber 45 along the ventilation passage 51, the air flowing into the ventilation passage 51 can be guided from the entire circumference of the inflow chamber 45 to the inflow chamber 45 through the shielding walls 48.

Therefore, the air uniformly flows into the inflow chamber 45 and the reliability in optically detecting the smoke contained in the air is improved.

Third Embodiment

Figure 20:
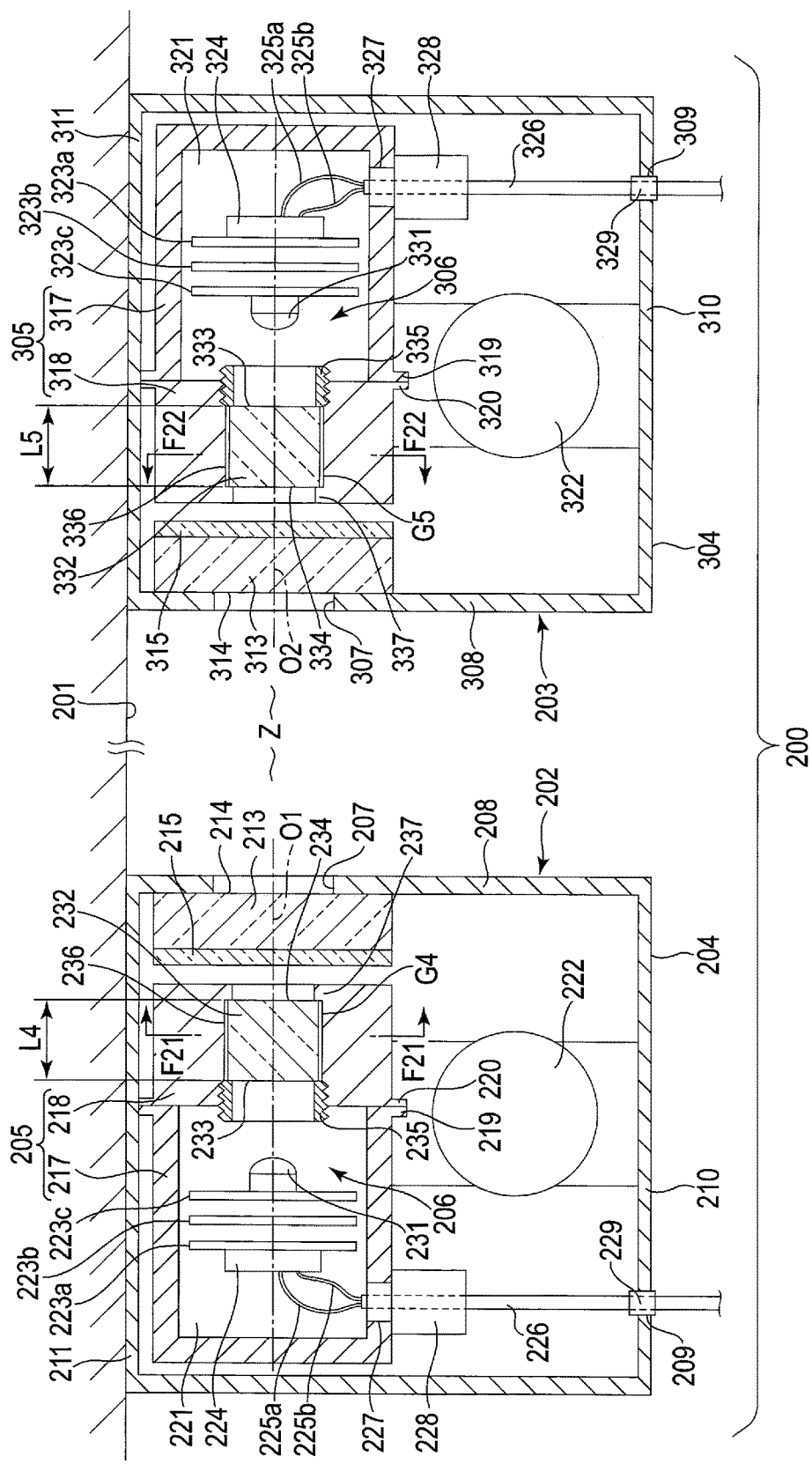
FIG. 20 is a cross-sectional view showing a separation type photoelectric smoke sensor according to a Third Embodiment installed on a ceiling surface of a building.
Figure 21:
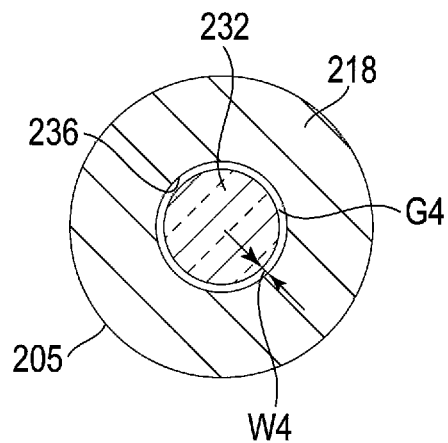
FIG. 21 is a cross-sectional view seen along line F21-F21 of FIG. 20.
Figure 22:
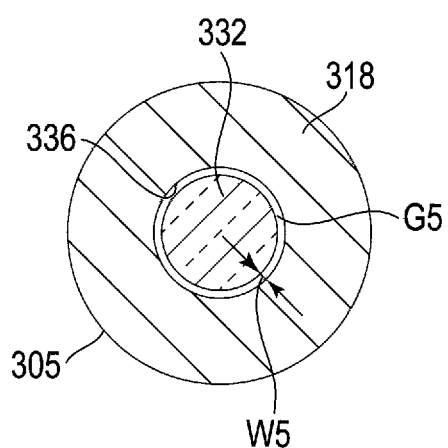
FIG. 22 is a cross-sectional view seen along line F22-F22 of FIG. 20.

FIG. 20 to FIG. 22 disclose a Third Embodiment. FIG. 20 shows a state in which a separation type photoelectric smoke sensor 200 is installed on a ceiling surface 201 of a building. The photoelectric smoke sensor 200 comprises a light emitting unit 202 and a light receiving unit 203 which are independent of each other. Each of the light emitting unit 202 and the light receiving unit 203 is an example of an optical unit. The light emitting unit 202 and the light receiving unit 203 are exposed in a designated explosion-proof zone Z in the building and face each other while spaced apart.

As shown in FIG. 20, the light emitting unit 202 comprises a protective member 204, a housing 205, and a light emitting portion 206 as main elements. The protective member 204 is, for example, a rectangular box-shaped element and comprises a front plate 208 having a light irradiation hole 207 opened, a bottom plate 210 having a through hole 209 opened, and a top plate 211 directly attached to the ceiling surface 201. The protective member 204 is formed of, for example, a metal material such as iron-aluminum alloy or a resin material such as engineering plastic, and has a strength compatible with the explosion-proof standard. Furthermore, the protective member 204 is preferably formed of a metal material rather than a resin material from the viewpoint of prevention of the generation of static electricity.

The light irradiation hole 207 of the protective member 204 is covered with a protective glass 213 from the inside of the protective member 204. The protective glass 213 is a rectangular plate-like element formed of, for example, tempered glass and is fixed to the inner surface of the front plate 208 of the protective member 204 to close the light irradiation hole 207. The protective glass 213 has a light exit surface 214 exposed to the designated explosion-proof zone Z through the light irradiation hole 207.

A polarizer 215 is stacked on a surface of the protective glass 213 opposite to the light emitting surface 214. The polarizer 215 is a rectangular plate-like element formed of, for example, a polarizing glass or a polarizing film and is accommodated inside the protective member 204.

The housing 205 comprises a main body 217 and a support body 218. The main body 217 is a cylindrical element having one end closed, and a first flange portion 219 continuous in the circumferential direction is formed at the opening end of the main body 217. The support body 218 is a cylindrical element thicker than the main body 217, and a second flange portion 220 continuous in the circumferential direction is formed at one end portion of the support portion 218. The first flange portion 219 and the second flange portion 220 are integrally coupled to each other via, for example, a plurality of clamps such as bolts and nuts, in a state of abutting on each other. The main body 217 and the support body 218 are coaxially connected and a circuit accommodation chamber 221 is formed inside the main body 217, by this coupling.

The main body 217 and the support body 218 cooperate with each other to form the cylindrical housing 205 having an axis O1. The axis O1 extends in the lateral direction through the center of the housing 205.

The housing 205 is accommodated inside the protective member 204 via an angle adjustment mechanism 222. The angle adjustment mechanism 222 is an element for finely adjusting the angle of the axis O1 of the housing 205 with respect to the horizontal line and is interposed between the bottom plate 210 of the protective member 204 and the housing 205.

According to the present embodiment, the housing 205 has an explosion-proof structure which enables the housing 205 to withstand the explosion pressure even when the combustible gas explodes in the circuit accommodation chamber 221. Furthermore, the first flange portion 219 and the second flange portion 220 are brought into surface contact with each other and a sealing surface is formed between the first flange portion 219 and the second flange portion 220, in a state in which the main body 217 and the support body 218 are coupled to each other.

In the present embodiment, the sealing surface is formed between the first flange portion 219 of the main body 217 and the second flange portion 220 of the support body 218, but the main body 217 and the support body 218 may be formed as an integral structure and the sealing surface may not be formed.

As shown in FIG. 20, a plurality of circuit boards 223a, 223b, and 223c are accommodated in the circuit accommodation chamber 221. The circuit boards 223a, 223b, and 223c are arranged at intervals in the direction of the axis O1 passing through the center of the housing 205.

A terminal block 224 is electrically connected to the circuit board 223a. A plurality of cables 225a and 225b are connected to the terminal block 224. The cables 225a and 225b are drawn from the circuit accommodation chamber 221 to the designated explosion-proof zone Z via a cylindrical cable guide 226 and are also connected to, for example, an external device such as an external power supply.

The cable guide 226 is guided to the inside of the protective member 204 through a guide hole 227 formed in the peripheral wall of the main body 217 and also guided to the designated explosion-proof zone Z through the through hole 209 of the protective member 204. In the present embodiment, a cable gland 228 is inserted into the guide hole 227. Furthermore, a cylindrical plug body 229 is inserted into the through hole 209. For this reason, the cable guide 226 penetrates the cable gland 228 and the plug body 229 and is guided from the housing 205 to the designated explosion-proof zone Z.

A gap allowing insertion of the cable gland 228 exists between the guide hole 227 of the housing 205 and the cable gland 228. The size of the gap and the length of the gap along the thickness direction of the peripheral wall of the main body 217 are set to values conforming to the explosion-proof standard. If the size and the length of the gap conform to the explosion-proof standard, the flame caused by the explosion in the circuit accommodation chamber 221 may reach the gap but the escape of the flame flowing from the circuit accommodation chamber 221 to the inside of the protective member 204 through the gap can be prevented.

The size and length of the gap are varied according to the gas atmosphere of the designated explosion-proof zone Z where the photoelectric smoke sensor 200 is installed, the volume of the circuit accommodation chamber 221, and the like. More specifically, the size of the gap may be set to, for example, at most 0.3 mm, preferably at most 0.1 mm. The smaller size of the gap is preferable but the size exceeds 0 mm from the viewpoint of manufacturing.

The length of the gap differs according to the size of the gap. The length of the gap may be set to, for example, at least 9.5 mm, preferably at least 40 mm, and the longer gap length is preferable. The flame generated in the circuit accommodation chamber 221 does not leak out of the housing 205 along the gap by making the size and length of the gap conform to the explosion-proof standard.

As shown in FIG. 20, the light emitting portion 206 is accommodated in the housing 205. The light emitting portion 206 comprises a light emitting diode 231 and a first light guide 232 as main elements. The light-emitting diode 231 is an example of a light emitting element and is mounted in the center of the circuit board 223c. The light emitting diode 231 is directed to the light irradiation hole 207 of the protective member 204 on the axis O1 of the housing 205.

Preferably, the first light guide 232 is an element for guiding the light emitted from the light emitting diode 231, to the light irradiation hole 207 of the protective member 204, via the polarizer 215 and the protective glass 213 and is shaped to converge light and formed of a material which converges light. According to the present embodiment, the first light guide 232 is formed of, for example, a columnar colorless and transparent glass. The first light guide 232 has a flat light receiving surface 233 facing the light emitting diode 231 and a flat light emitting surface 234 facing the polarizer 215. The light receiving surface 233 and the light emitting surface 234 are separated from each other in the axial direction of the first light guide 232.

As shown in FIG. 20, the first light guide 232 is held coaxially with the support body 218 of the housing 205 via a fixing member 235. More specifically, the cylindrical support body 218 has an inner wall surface 236 surrounding the first light guide 232. A stopper portion 237 continuous in the circumferential direction is formed at one end portion of the inner wall surface 236 which faces the polarizer 215. The stopper portion 237 protrudes inside the inner wall surface 236 such that the outer peripheral portion of the light emitting surface 234 of the first light guide 232 abuts on the stopper portion 237.

The fixing portion 235 is a hollow cylindrical element and has an outer diameter larger than that of the first light guide 232 and an inner diameter smaller than the outer diameter of the first light guide 232. The fixing member 235 is screwed into the other end portion of the inner wall surface 236 of the support body 218, which faces the circuit accommodation chamber 221. The threaded end of the fixing member 235 abuts on the outer peripheral portion of the light receiving surface 233 of the first light guide 232, and cooperates with the stopper portion 237 to sandwich the first light guide 232 in the axial direction, by this screwing.

The light receiving surface 233 is exposed to the circuit accommodation chamber 221 so as to face the light emitting diode 231, and the light emitting surface 234 is exposed to the inside of the protective member 204 so as to face the polarizer 215, in a state where the first light guide 232 is held by the support body 218.

As shown in FIG. 20 and FIG. 21, a first gap G4 allowing the first light guide 232 to be fitted is provided between the outer peripheral surface of the first light guide 232 and the inner wall surface 236 of the support body 218. The first gap G4 communicates with both of the inside of the circuit accommodation chamber 221 and the inside of the protective member 204.

The size W4 of the first gap G4 can be restated as a distance from an arbitrary point on the inner wall surface 236 to the outer peripheral surface of the first light guide 232 distant in the radial direction of the first light guide 232 when the support body 218 and the first light guide 232 are coaxial. The length L4 along the depth direction of the first gap G4 is equal to the total length of the first light guide 232 from the light receiving surface 233 of the first light guide 232 to the light emitting surface 234.

Each of the size W4 and the length L4 of the first gap G4 is set to a value conforming to the explosion-proof standard. If the size W4 and the length L4 of the first gap G4 conform to the explosion proof standard, the flame caused by the explosion in the circuit accommodation chamber 221 may reach the first gap G4 but the escape of the flame to the inside of the protective member 204 through the first gap G4 can be prevented.

The size W4 and the length L4 of the first gap G4 are varied according to the gas atmosphere of the designated explosion-proof zone Z in which the photoelectric smoke sensor 200 is installed, the volume of the circuit accommodation chamber 221, and the like. The size W4 of the first gap G4 may be set to, for example, at most 0.3 mm, preferably at most 0.1 mm. The smaller size W4 of the first gap G4 is preferable but the size exceeds 0 mm from the viewpoint of manufacturing.

The length L4 of the first gap G4 differs according to the size W4 of the first gap G4. The length L4 of the first gap G4 may be set to at least 9.5 mm, preferably at least 40 mm, and the longer length L4 of the first gap G4 is preferable.

If the center of the support body 218 does not coincide with the center of the first light guide 232 and the size W4 of the first gap G4 is not uniform along the circumferential direction of the second light guide 232, the maximum value of the size W4 of the first gap G4 may be 0.3 mm or less, preferably 0.1 mm or less.

In contrast, the light receiving unit 203 of the photoelectric smoke sensor 200 basically has the same configuration as that of the light emitting unit 202. More specifically, the light receiving unit 203 comprises a protective member 304, a housing 305, and a light receiving portion 306 as main elements as shown in FIG. 20.

The protective member 304 is, for example, a rectangular box-shaped element and comprises a front plate 308 having a light incident hole 307 opened, a bottom plate 310 having a through hole 309 opened, a top plate 311 attached directly to the ceiling surface 201 of the building. The protective portion 304 is formed of, for example, a metal material such as iron-aluminum alloy or a resin material such as engineering plastic, and has a strength conforming to the explosion-proof standard. Furthermore, the protective portion 304 is preferably formed of a metal material rather than a resin material, from the viewpoint of preventing generation of static electricity.

The light incident hole 307 of the protective member 304 is covered with protective glass 313 from the inside of the protective member 304. The protective glass 313 is, for example, a square plate-shaped element formed of tempered glass and is fixed to the inner surface of the front plate 308 of the protective member 304 so as to close the light incident hole 307. The protective glass 313 has a light incident surface 314 exposed to the designated explosion-proof zone Z through the light incident hole 307.

A polarizer 315 is stacked on a surface of the protective glass 313 opposite to the light incident surface 314. The polarizer 315 is, for example, a rectangular plate-like element composed of polarizing glass and a polarizing film, and is accommodated inside the protective member 304.

The housing 305 comprises a main body 317 and a support body 318. The main body 317 is a cylindrical element having one end closed, and a first flange portion 319 continuous in the circumferential direction is formed at the opening end of the main body 317. The support body 318 is a cylindrical element thicker than the main body 317, and a second flange portion 320 continuous in the circumferential direction is formed at one end portion of the support portion 318. The first flange portion 319 and the second flange portion 320 are integrally coupled to each other via, for example, a plurality of clamps such as bolts and nuts, in a state of abutting on each other. The main body 317 and the support body 318 are coaxially connected and a circuit accommodation chamber 321 is formed inside the main body 317, by this coupling.

The main body 317 and the support body 318 cooperate with each other to form the cylindrical housing 305 having an axis O2. The axis O2 extends in the lateral direction through the center of the housing 305.

The housing 305 is accommodated inside the protective member 304 via an angle adjustment mechanism 322. The angle adjustment mechanism 322 is an element for finely adjusting the angle of the axis O2 of the housing 305 with respect to the horizontal line and is interposed between the bottom plate 310 of the protective member 304 and the housing 305.

According to the present embodiment, the housing 305 has an explosion-proof structure which enables the housing 305 to withstand the explosion pressure even if the combustible gas explodes in the circuit accommodation chamber 321. Furthermore, the first flange portion 319 and the second flange portion 320 are brought into surface contact with each other and a sealing surface is formed between the first flange portion 319 and the second flange portion 320, in a state in which the main body 317 and the support body 318 are coupled to each other.

In the present embodiment, the sealing surface is formed between the first flange portion 319 of the main body 317 and the second flange portion 320 of the support body 318, but the main body 317 and the support body 318 may be formed as an integral structure and the sealing surface may not be formed.

As shown in FIG. 20, a plurality of circuit boards 323a, 323b, and 323c are accommodated in the circuit accommodation chamber 321. The circuit boards 323a, 323b, and 323c are arranged at intervals in the direction of the axis O2 passing through the center of the housing 305.

A terminal block 324 is electrically connected to the circuit board 323a. A plurality of cables 325a and 325b are electrically connected to the terminal block 324. The cables 325a and 325b are drawn to the designated explosion-proof zone Z via a cylindrical cable guide 326 and are also connected to, for example, an external device such as an external power supply.

The cable guide 326 is guided to the inside of the protective member 304 through a guide hole 327 formed in the peripheral wall of the main body 317 and also guided to the designated explosion-proof zone Z through the through hole 309 of the protective member 304. In the present embodiment, a cable gland 328 is inserted into the guide hole 327. Furthermore, a cylindrical plug body 329 is inserted into the through hole 309. For this reason, the cable guide 326 penetrates the cable gland 328 and the plug body 329 and is guided from the housing 305 to the designated explosion-proof zone Z.

A gap allowing insertion of the cable gland 328 exists between the guide hole 327 of the housing 305 and the cable gland 328. The size of the gap and the length of the gap along the thickness direction of the peripheral wall of the main body 317 are set to values conforming to the explosion-proof standard. If the size and the length of the gap conform to the explosion-proof standard, the flame caused by the explosion in the circuit accommodation chamber 321 may reach the gap but the escape of the flame flowing from the circuit accommodation chamber 321 to the inside of the protective member 304 through the gap can be prevented. For this reason, the flame generated in the circuit accommodation chamber 321 does not leak out of the housing 305.

The size and length of the gap are varied according to the gas atmosphere of the designated explosion-proof zone Z where the photoelectric smoke sensor 200 is installed, the volume of the circuit accommodation chamber 321, and the like. Concrete values of the size and length of the gap are the same as those of the light emitting unit 203 and their explanations are omitted.

As shown in FIG. 20, the light emitting potion 306 is accommodated in the housing 305. The light receiving portion 306 comprises a photodiode 331 and a second light guide 332 as main elements. The photodiode 331 is an example of a light receiving element and is mounted in the center of the circuit board 323c. The photodiode 331 is directed to the light incident hole 307 of the protective member 304 on the axis O2 of the housing 305.

Preferably, the second light guide 332 is an element for guiding the light emitted from the light emitting diode 231 of the light emitting unit 202, from the light incident hole 307 to the photodiode 331 via the protective glass 313 and the polarizer 315 and is shaped to converge light and formed of a material which converges light. According to the present embodiment, the second light guide 332 is formed of, for example, a columnar colorless and transparent glass. The second light guide 332 has a flat light emitting surface 333 facing the photodiode 331 and a flat light receiving surface 334 facing the polarizer 315. The light emitting surface 333 and the light receiving surface 334 are separated from each other in the axial direction of the second light guide 332.

As shown in FIG. 20, the second light guide 332 is held coaxially with the support body 318 of the housing 305 via a fixing member 335. More specifically, the cylindrical support body 318 has an inner wall surface 336 surrounding the second light guide 331. A stopper portion 337 continuous in the circumferential direction is formed at one end portion of the inner wall surface 336 which faces the polarizer 315. The stopper portion 337 protrudes inside the inner wall surface 336 such that the outer peripheral portion of the light emitting surface 334 of the second light guide 332 abuts on the stopper portion 337.

The fixing member 335 is a hollow cylindrical element and has an outer diameter larger than that of the second light guide 332 and an inner diameter smaller than the outer diameter of the first light guide 332. The fixing member 335 is screwed into the other end portion of the inner wall surface 336 of the support body 318, which faces the circuit accommodation chamber 321. The threaded end of the fixing member 335 abuts on the outer peripheral portion of the light emitting surface 333 of the second light guide 332, and cooperates with the stopper portion 337 to sandwich the second light guide 332 in the axial direction, by this screwing.

The light emitting surface 333 is exposed to the circuit accommodation chamber 321 so as to face the photodiode 331, and the light receiving surface 334 is exposed to the inside of the protective member 304 so as to face the polarizer 315, in a state where the second light guide 332 is held by the support body 318.

As shown in FIG. 20 and FIG. 22, a second gap G5 allowing the second light guide 332 to be fitted is provided between the outer peripheral surface of the second light guide 332 and the inner wall surface 336 of the support body 318. The second gap G5 communicates with both of the inside of the circuit accommodation chamber 321 and the inside of the protective member 304.

The size W5 of the second gap G5 can be restated as a distance from an arbitrary point on the inner wall surface 336 to the outer peripheral surface of the second light guide 332 distant in the radial direction of the second light guide 332 when the support body 318 and the second light guide 332 are coaxial. The length L5 along the depth direction of the second gap G5 is equal to the total length of the second light guide 332 from the light emitting surface 333 of the second light guide 332 to the light receiving surface 334.

Each of the size W5 and the length L5 of the second gap G5 is set to a value conforming to the explosion-proof standard. If the size W5 and the length L5 of the second gap G5 conform to the explosion proof standard, the flame caused by the explosion in the circuit accommodation chamber 321 may reach the second gap G5 but the escape of the flame to the inside of the protective member 304 through the second gap G5 can be prevented.

The size W5 and the length L5 of the second gap G5 are varied according to the gas atmosphere of the designated explosion-proof zone Z in which the photoelectric smoke sensor 200 is installed, the volume of the circuit accommodation chamber 321, and the like. Since concrete values of the size W5 and the length L5 of the second gap G5 are the same as the size W4 and the length L4 of the first gap G4 of the light emitting unit 202, their explanations are omitted.

Next, the operations of the separation type photoelectric smoke sensor 200 will be described.

As shown in FIG. 20, the separation type photoelectric smoke sensor 200 is installed on the ceiling surface 201 of a building such that the light irradiation hole 207 of the light emitting unit 202 and the light incident hole 307 of the light receiving unit 203 face each other in the designated explosion-proof zone Z.

Since the separation type photoelectric smoke sensor 200 has a large occupation area as compared with the integration type photoelectric smoke sensor 1 disclosed in the First Embodiment but can easily sense smoke, the smoke sensor is suitable for use in, for example, a high ceiling warehouse or an oil refining factory.

The separation type photoelectric smoke sensor 200 is not limited to use in an attitude fixed on the ceiling surface 201. For example, the light emitting unit 202 may be used such that a back surface of the housing 205 located behind the light irradiation hole 207 is fixed to a side wall surface of the building, and the light receiving unit 203 may be used such that a back surface of the housing 305 located behind the light incident surface 307 is fixed to the side wall surface of the building.

When the photoelectric smoke sensor 200 is in operation, the light emitted from the light emitting diode 231 of the light emitting unit 202 is made incident on the light receiving surface 233 of the first light guide 232. Part of the light incident on the light receiving surface 233 passes through the inside of the first light guide 232 in the axial direction and the remaining light travels toward the light emitting surface 234 while repeating total reflection on the outer peripheral surface of the first light guide 232.

The light reaching the light emitting surface 234 of the first light guide 232 is radiated toward the polarizer 215. The polarizer 215 changes the light radiated from the light emitting surface 234 into a light wave which oscillates in a certain direction alone. The light passing through the polarizer 215 is irradiated from the light irradiation surface 214 of the protective glass 213 to the designated explosion-proof zone Z.

The light irradiated in the designated explosion-proof zone Z is made incident on the light incident surface 314 of the protective glass 313 of the light receiving unit 203 and then incident on the light receiving surface 334 of the second light guide 332 through the polarizer 315. Part of the light incident on the light receiving surface 334 passes through the inside of the second light guide 332 in the axial direction and the remaining light travels toward the light emitting surface 333 while repeating total reflection on the outer peripheral surface of the second light guide 332.

The light reaching the light emitting surface 333 of the second light guide 332 is emitted toward the photodiode 331, and the photodiode 331 detects the light. As a result, an electric signal indicating that the light has been detected is sent from the photodiode 331 to the circuit board 323c.

The light emitted by the light emitting unit 202 is guided to the light receiving unit 203 without being disturbed, at an ordinary time at which smoke is not included in the air of the designated explosion-proof zone Z. In contrast, if smoke is included in the air of the designated explosion-proof zone Z, the light emitted by the light emitting unit 202 is scattered by the smoke and the quantity of the light incident on the photodiode 331 of the light receiving unit 203 is reduced. For this reason, an electric signal indicating that the light amount has reduced is sent from the photodiode 331 to the circuit board 323c. The circuit board 323c outputs an electric signal to inform the outside that smoke has occurred in the designated explosion-proof zone Z.

More specifically, an electric signal may be sent to a buzzer provided outside to sound a buzzer or the color of light emitted by the indicator lamp provided outside may be changed.

According to the present embodiment, if combustible gas exists in the designated explosion-proof zone Z the combustible gas may enter the light emitting unit 202 and the light receiving unit 203 since both of the light emitting unit 202 and the light receiving unit 203 are exposed in the designated explosion-proof zone Z.

More specifically, in the light emitting unit 202, combustible gas enters the inside of the protective member 204 through the gap between the through hole 209 of the protective member 204 and the plug body 229, and the gap between the protective member 204 and the protective glass 213 from the light irradiation hole 207. The combustible gas which has entered the inside of the protective member 204 cannot be avoided from entering the circuit accommodation chamber 221 in the housing 205 through the gap between the guide hole 227 of the housing 205 and the cable gland 228, the gap between the first flange portion 219 of the main body 217 and the second flange portion 220 of the support body 218, and the first gap G3 between the outer peripheral surface of the first light guide 232 and the inner peripheral surface 236 of the support body 218.

The combustible gas which has entered the circuit accommodation chamber 221 may cause an explosion, for example, when a spark resulting from a short current generated on the surfaces of the circuit boards 223a, 223b, and 223c or an abnormal high temperature part occurs on the surfaces of the circuit boards 223a, 223b, and 223c.

According to the present embodiment, the housing 205 defining the circuit accommodation chamber 221 can sufficiently withstand the explosion in the circuit accommodation chamber 221 without being damaged since the housing 205 has a pressure-resistant explosion-proof structure. The flame generated by the explosion in the circuit accommodation chamber 221 is therefore confined inside the housing 205 and does not leak out to the inside of the protective member 204 or the designated explosion-proof zone Z.

In contrast, the flame generated by the explosion in the circuit accommodation chamber 221 passes through the inside of the cylindrical fixing member 235 and reaches the first gap G4 between the outer peripheral surface of the first light guide 232 and the inner wall surface 236 of the support body 218. The flame which has reached the first gap G4 travels toward the light emitting surface 234 of the first light guide 232 along the first gap G4.

According to the present embodiment, the size W4 and the length L4 of the first gap G4 are set to values conforming to the explosion-proof standard. For this reason, the flame which has reached the first gap G4 naturally disappears in the course of traveling through the first gap G4, and ejection of the flame from the first gap G4 toward the inside of the protective member 204 can be avoided.

In the light receiving unit 203, combustible gas enters the inside of the protective member 304 through the gap between the through hole 309 of the protective member 304 and the plug body 329, and the gap between the protective member 304 and the protective glass 313 from the light incident hole 307. The combustible gas which has entered the inside of the protective member 304 cannot be avoided from entering the circuit accommodation chamber 321 in the housing 305 through the gap between the guide hole 327 of the housing 305 and the cable gland 328, the gap between the first flange portion 319 of the main body 317 and the second flange portion 320 of the support body 318, and the second gap G5 between the outer peripheral surface of the second light guide 332 and the inner peripheral surface 336 of the support body 318.

The combustible gas which has entered the circuit accommodation chamber 321 may cause an explosion, for example, when a spark resulting from a short current generated on the surfaces of the circuit boards 323a, 323b, and 323c or an abnormal high temperature part occurs on the surfaces of the circuit boards 323a, 323b, and 323c.

According to the present embodiment, the housing 305 defining the circuit accommodation chamber 321 can sufficiently withstand the explosion in the circuit accommodation chamber 321 without being damaged since the housing 305 has a pressure-resistant explosion-proof structure. The flame generated by the explosion in the circuit accommodation chamber 321 is therefore confined inside the housing 305 and does not leak out to the inside of the protective member 304 or the designated explosion-proof zone Z.

In contrast, the flame generated by the explosion in the circuit accommodation chamber 321 passes through the inside of the cylindrical fixing member 335 and reaches the second gap G5 between the outer peripheral surface of the second light guide 332 and the inner wall surface 336 of the support body 318. The flame which has reached the second gap G5 travels toward the light receiving surface 334 of the second light guide 332 along the second gap G5.

According to the present embodiment, the size W5 and the length L5 of the second gap G5 are set to values conforming to the explosion-proof standard. For this reason, the flame which has reached the second gap G5 naturally disappear in the course of traveling through the second gap G5, and ejection of the flame from the second gap G5 toward the inside of the protective member 304 can be avoided.

Thus, according to the present embodiment, the flame generated in the circuit accommodation chamber 221 of the light emitting unit 202 and the circuit accommodation chamber 321 of the light receiving unit 203 does not ignite combustible gas, and the explosion accident in the designated explosion-proof zone Z can be prevented preliminarily.

Furthermore, since the first gap G4 and the second gap G5 do not need to be filled with the sealant formed of resin, inconvenience that the flame generated in the circuit accommodation chambers 221 and 321 through the cracks and holes due to aged deterioration of the sealant may leak out into the designated explosion-proof zone Z can be solved. The flame generated in the circuit accommodation chambers 221 and 321 therefore does not ignite the explosive gas outside the photoelectric smoke sensor 200.

In addition, according to the present embodiment, the angle of the housing 205 incorporating the light emitting portion 206 can be finely adjusted by the angle adjustment mechanism 222, in the light emitting unit 202. Similarly, the angle of the housing 305 incorporating the light receiving portion 306 can be finely adjusted by the angle adjustment mechanism 322, in the light receiving unit 203, too. For this reason, the attitude of the housings 205 and 305 can be adjusted such that the axis O1 of the housing 205 and the axis O2 of the housing 305 are located on the same straight line.

Therefore, the light emitted from the light emitting unit 202 can be certainly received and whether smoke is contained in the air in the designated explosion-proof zone Z or not can be detected optically and accurately.

Fourth Embodiment

Figure 23:
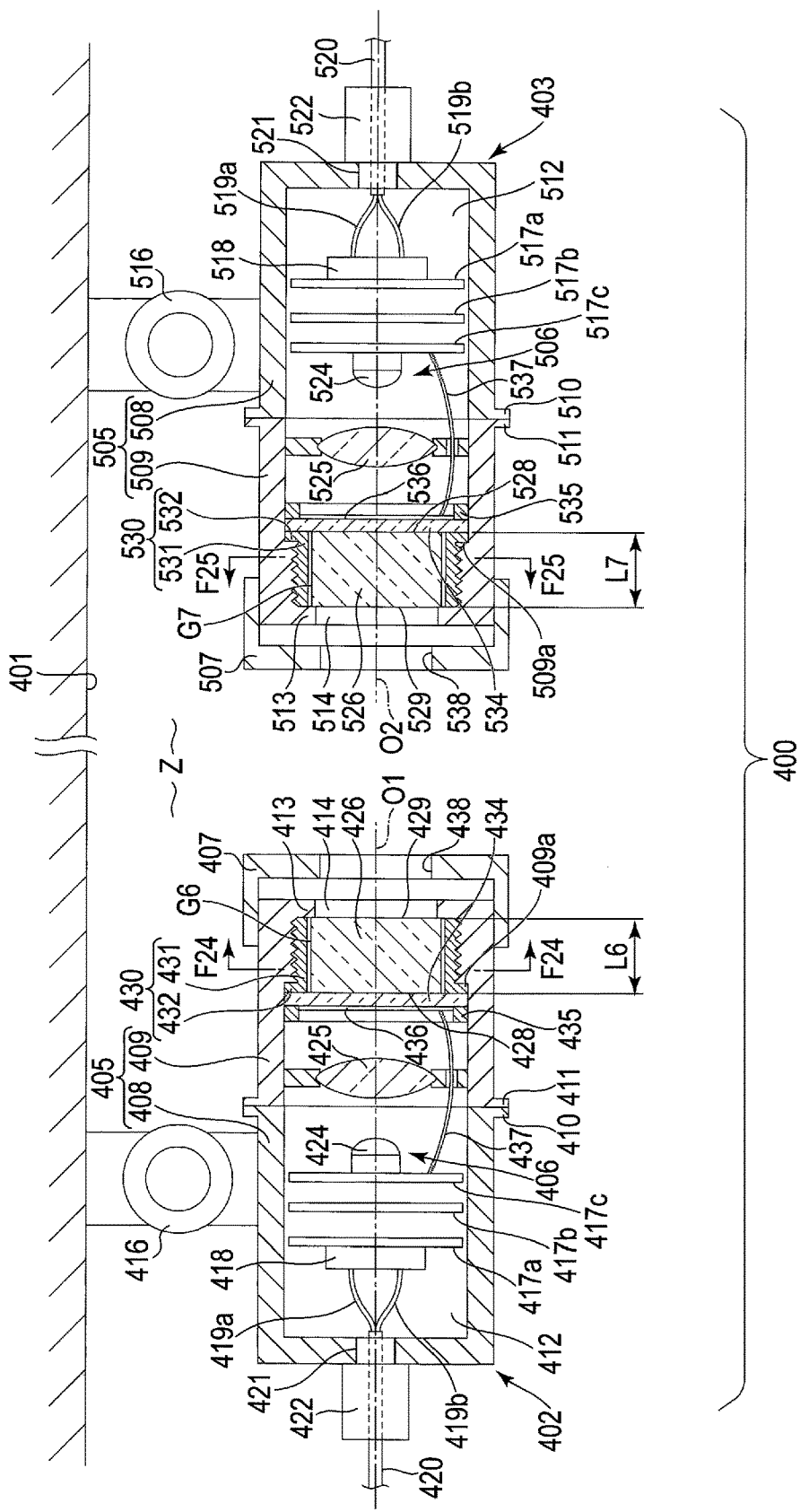
FIG. 23 is a cross-sectional view showing a separation type photoelectric smoke sensor according to a Fourth Embodiment installed on a ceiling surface of a building.
Figure 24:
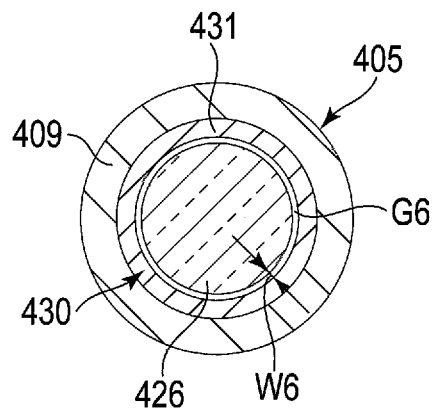
FIG. 24 is a cross-sectional view seen along line F24-F24 of FIG. 23.
Figure 25:
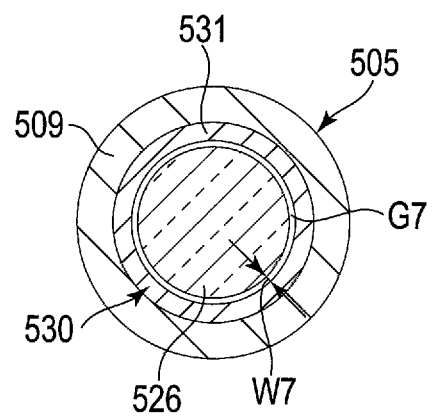
FIG. 25 is a cross-sectional view seen along line F25-F25 of FIG. 23.

FIG. 23 to FIG. 25 disclose a Fourth Embodiment relating to a separation type photoelectric smoke sensor 400. FIG. 23 shows a state in which a separation type photoelectric smoke sensor 400 is installed on a ceiling surface 401 of a building. The photoelectric smoke sensor 400 comprises a light emitting unit 402 and a light receiving unit 403 which are independent of each other. Each of the light emitting unit 402 and the light receiving unit 403 is an example of an optical unit. The light emitting unit 402 and the light receiving unit 403 are exposed in a designated explosion-proof zone Z in the building and face each other while spaced apart.

As shown in FIG. 23, the light emitting unit 402 comprises a housing 405, a light emitting portion 406, and a protective member 407 as main elements. The housing 405 comprises a main body 408 and a support body 409. The main body 408 is a cylindrical element having one end closed, and a first flange portion 410 continuous in the circumferential direction is formed at the opening end of the main body 408. The support body 409 is a cylindrical element having the same diameter as the housing 405, and a second flange portion 411 continuous in the circumferential direction is formed at one end portion of the support portion 409. The first flange portion 410 and the second flange portion 411 are integrally coupled to each other via, for example, a plurality of clamps such as bolts and nuts, in a state of abutting on each other.

The main body 408 and the support body 409 are coaxially connected and a circuit accommodation chamber 412 is formed inside the main body 408, by this coupling. Furthermore, the main body 408 and the support body 409 cooperate with each other to form the cylindrical housing 405 having an axis O1. The axis O1 extends in the lateral direction through the center of the housing 405.

A stopper portion 413 is formed at the other portion on a side opposite to the main body 408 of the support body 409. The stopper portion 413 is continuous in the circumferential direction of the support body 409 and expands to the inside in the radial direction of the support body 409. The stopper portion 413 defines a light irradiation hole 414 at the other end portion of the support body 409. The axis O1 of the housing 405 coaxially penetrates the light irradiation hole 414.

The housing 405 is supported on the ceiling surface 401 of the building via an angle adjustment mechanism 416. The angle adjustment mechanism 416 is an element for finely adjusting the angle of the axis O1 of the housing 205 with respect to the horizontal line. The angle adjustment mechanism 416 is interposed between the ceiling surface 401 and the main body 408 of the housing 405. The angle adjustment mechanism 416 is not limited to fixation on the ceiling surface 401, but can be fixed on, for example, a place where the photoelectric smoke sensor 400 should be installed, such as a side wall surface, a pillar, a beam or the like of the building.

According to the present embodiment, the housing 405 has an explosion-proof structure capable of withstanding the explosion pressure even if the combustible gas explodes in the circuit accommodation chamber 412. Furthermore, the first flange portion 410 and the second flange portion 411 are brought into surface contact with each other and a sealing surface is formed between the first flange portion 410 and the second flange portion 411, in a state in which the main body 408 and the support body 409 are coupled to each other.

In the present embodiment, the sealing surface is formed between the first flange portion 410 of the main body 408 and the second flange portion 411 of the support body 409, but the main body 408 and the support body 409 may be formed as an integral structure and the sealing surface may not be formed.

As shown in FIG. 23, a plurality of circuit boards 417a, 417b, and 417c are accommodated in the circuit accommodation chamber 412. The circuit boards 417a, 417b, and 417c are arranged at intervals in the direction of the axis O1 passing through the center of the housing 405.

A terminal block 418 is electrically connected to the circuit board 417a. A plurality of cables 419a and 419b are connected to the terminal block 418. The cables 419a and 419b are drawn from the circuit accommodation chamber 412 to the designated explosion-proof zone Z via a cylindrical cable guide 420 and are also connected to, for example, an external device such as an external power supply.

The cable guide 420 penetrates a guide hole 421 opened on the end wall of the main body 408 and is guided to the designated explosion-proof zone Z. In the present embodiment, a cable gland 422 is inserted into the guide hole 421. The cable guide 420 is drawn from the circuit accommodation chamber 412 to the outside of the housing 405 through the cable gland 422.

A gap allowing insertion of the cable gland 422 exists between the guide hole 421 of the main body 408 and the cable gland 422. The size of the gap and the length of the gap along the thickness direction of the end wall of the main body 408 are set to values conforming to the explosion-proof standard. When the size and the length of the gap conform to the explosion-proof standard, the escape of the flame flowing to the designated explosion-proof zone Z through the gap can be prevented even if the flame caused by the explosion in the circuit accommodation chamber 412 reaches the gap.

As shown in FIG. 23, the light emitting portion 406 is accommodated in the housing 405. The light emitting portion 406 comprises a light emitting diode 424, an optical lens 425, and a first light guide 426 as main elements. The light emitting diode 424 is an example of a light emitting element. The light emitting diode 424 is mounted on a central portion of the circuit board 417c and directed to the light irradiation hole 414 on the axis O1 of the housing 405.

The optical lens 425 is formed of, for example, glass and has a shape similar to a convex lens. The optical lens 425 is held on the inner peripheral surface of an end portion of the support body 409 so as to face the light emitting diode 424.

The first light guide 426 is formed of, for example, a columnar, colorless and transparent glass. The first light guide 426 has a flat light receiving surface 428 facing the optical lens 425 and a flat light emitting surface 429 exposed to the designated explosion-proof zone Z through the light irradiation hole 414. The light receiving surface 428 and the light emitting surface 429 are separated from each other in the axial direction of the first light guide 426.

According to the present embodiment, the first light guide 426 is coaxially held in the support body 409 via a first holder 430. More specifically, the first holder 430 is formed of, for example, a metal material such as an aluminum alloy. The first holder 430 comprises a cylindrical portion 431 in which the first light guide 426 is coaxially fitted and a flange portion 432 formed on one end of the cylindrical portion 431. The flange portion 432 expands to the outside of the radial direction of the cylindrical portion 431.

The cylindrical portion 431 is screwed into the inside of the support body 409 from the direction of the main body 408. A tip of the cylindrical portion 431 on the side opposite to the flange portion 432 and an outer peripheral portion of the light emitting surface 429 of the first light guide 426 abut on the stopper portion 413 of the support body 409, by this screwing. Simultaneously, the flange portion 432 abuts on a step portion 409a of the inner peripheral surface of the support body 409. As a result, the first light guide 426 is held at a fixed position inside the support body 409.

As shown in FIG. 23, the light receiving surface 428 of the first light guide 426 faces the optical lens 425, and the light emitting surface 429 of the first light guide 426 is exposed to the designated explosion-proof zone Z through the light irradiation hole 414, in a state where the first light guide 426 is held inside the support body 409.

According to the present embodiment, the light receiving surface 428 of the first light guide 426 is covered with a polarizer 434. The polarizer 434 is, for example, a disc-like element composed of polarizing glass and a polarizing film, and is held inside the support body 409 via a fixing ring 435. The fixing ring 435 is inserted into the support body 409 from the direction of the main body 408 and the outer peripheral portion of the polarizer 434 is sandwiched between the fixing ring 435 and the flange portion 432 of the first holder 430.

Furthermore, a heater 436 for prevention of dew condensation is disposed inside the fixing ring 435. The heater 436 is an element for preventing the function of the polarizer 434 from decreasing due to dew condensation and is in contact with the polarizer 434. The heater 436 is electrically connected to the circuit board 417c via a lead 437.

As shown in FIG. 23 and FIG. 24, a first gap G6 allowing fitting of the first light guide 426 is provided between the outer peripheral surface of the first light guide 426 and the inner peripheral surface of the cylindrical portion 431 of the first holder 430. The first gap G6 communicates with the circuit accommodation chamber 412 inside the support 409 and also communicates with the designated explosion-proof zone Z through the light irradiation hole 414.

As shown in FIG. 24, when the first light guide 426 and the cylindrical portion 431 maintain the coaxiality, the size W6 of the first gap G6 can be restated as a distance from an arbitrary point on the inner peripheral surface of the cylindrical portion 431 to the outer peripheral surface of the first light guide 426 distant from the first light guide 426 in the radial direction. The length L6 along the depth direction of the first gap G6 is equal to the total length of the first light guide 426 from the outer peripheral edge of the light receiving surface 428 of the first light guide 426 to the outer peripheral edge of the light emitting surface 429.

Each of the size W6 and the length L6 of the first gap G6 is set to values conforming to the explosion-proof standard. If the size W6 and the length L6 of the first gap G6 conform to the explosion-proof standard, the flame caused by the explosion in the circuit accommodation chamber 412 may reach the first gap G6 beyond the optical lens 425 and the polarizer 434 but the escape of the flame toward the designated explosion-proof zone Z through the gap G6 can be prevented.

The size W6 and the length L6 of the first gap G6 are varied according to the gas atmosphere of the explosion-proof designated zone Z where the photoelectric smoke sensor 400 is installed, the volume of the circuit accommodation chamber 412, and the like. The size W6 of the first gap G6 may be set to, for example, at most 0.3 mm, preferably at most 0.1 mm. The smaller size W6 of the first gap G6 is preferable but the size exceeds 0 mm from the viewpoint of manufacturing.

The length L6 of the first gap G6 differs according to the size W6 of the first gap G6. The length L6 of the first gap G6 may be set to at least 9.5 mm, preferably at least 40 mm, and the longer length L6 of the first gap G6 is preferable.

If the center of the first light guide 426 does not coincide with the center of the cylindrical portion 431 and the size W6 of the first gap G6 is not uniform along the circumferential direction of the first light guide 426, the maximum value of the size W6 of the first gap G6 may be 0.3 mm or less, preferably 0.1 mm or less.

The protective member 407 is an element for protecting the light irradiation hole 414 of the housing 405 and the light emitting surface 429 of the first light guide 426 exposed from the light irradiation hole 414 from the external impact and has strength conforming to the explosion-proof standard. The protective member 407 covers an end portion of the support body 409 at which the light irradiation hole 414 is opened, from the outside. The protective member 407 has an opening portion 438 which faces the light irradiation hole 414.

In contrast, the light receiving unit 403 of the photoelectric smoke sensor 400 basically has the same configuration as that of the light emitting unit 402. More specifically, the light receiving unit 403 comprises a housing 505, a light receiving portion 506, and a protective member 507 as main components.

The housing 505 comprises a main body 508 and a support body 509. The main body 508 is a cylindrical element closed at one end, and a first flange portion 510 continuous in the circumferential direction is formed at an open end of the main body 508. The support body 509 is a cylindrical element having the same diameter as the main body 508, and a second flange portion 511 continuous in the circumferential direction is formed at one end portion of the support body 509. The first flange portion 510 and the second flange portion 511 are integrally coupled to each other via, for example, a plurality of clamps such as bolts and nuts, in a state of abutting on each other.

The main body 508 and the support body 509 are coaxially connected and the circuit accommodation chamber 512 is formed inside the main body 508, by this coupling. Furthermore, the main body 508 and the support body 509 cooperate with each other to form the cylindrical housing 505 having an axis O2. The axis O2 extends in the lateral direction through the center of the housing 505.

A stopper portion 513 is formed at the other end portion of the support body 509 on the side opposite to the main body 508. The stopper portion 513 is continuous in the circumferential direction of the support body 509 and expands to the inside in the radial direction of the support body 509. For this reason, the stopper portion 513 defines the light incident hole 514 at the other end portion of the support body 509. The axis O2 of the housing 505 coaxially penetrates the light incident hole 514.

The housing 505 is supported on the ceiling surface 401 of the building via an angle adjustment mechanism 516. The angle adjustment mechanism 516 is an element for finely adjusting the angle of the axis O2 of the housing 505 with respect to the horizontal line. The angle adjustment mechanism 516 is interposed between the ceiling surface 401 and the main body 508 of the housing 505.

The angle adjustment mechanism 516 is not limited to fixation on the ceiling surface 401, but can be fixed on, for example, a place where the photoelectric smoke sensor 400 should be installed, such as a side wall surface, a pillar, a beam or the like of the building.

According to the present embodiment, the housing 505 has an explosion-proof structure capable of withstanding the explosion pressure even if the combustible gas explodes in the circuit accommodation chamber 512. Furthermore, the first flange portion 510 and the second flange portion 511 are brought into surface contact with each other and a sealing surface is formed between the first flange portion 510 and the second flange portion 511, in a state in which the main body 508 and the support body 509 are coupled to each other.

In the present embodiment, the sealing surface is formed between the first flange portion 510 of the main body 508 and the second flange portion 511 of the support body 509, but the main body 508 and the support body 509 may be formed as an integral structure and the sealing surface may not be formed.

As shown in FIG. 23, a plurality of circuit boards 517a, 517b, and 517c are accommodated in the circuit accommodation chamber 512. The circuit boards 517a, 517b, and 517c are arranged at intervals in the direction of the axis O2 passing through the center of the housing 505.

A terminal block 518 is electrically connected to the circuit board 517a. A plurality of cables 519a and 519b are connected to the terminal block 518. The cables 519a and 519b are drawn from the circuit accommodation chamber 512 to the designated explosion-proof zone Z via a cylindrical cable guide 520 and are also connected to, for example, an external device such as an external power supply.

The cable guide 520 penetrates a guide hole 521 opened on the end wall of the main body 508 and is guided to the designated explosion-proof zone Z. In the present embodiment, a cable gland 522 is inserted into the guide hole 521. The cable guide 520 is drawn from the circuit accommodation chamber 512 to the outside of the housing 505 through the cable gland 522.

A gap allowing insertion of the cable gland 522 exists between the guide hole 521 of the main body 508 and the cable gland 522. The size of the gap and the length of the gap along the thickness direction of the end wall of the main body 508 are set to values conforming to the explosion-proof standard. If the size and the length of the gap conform to the explosion-proof standard, the flame caused by the explosion in the circuit accommodating chamber 512 may reach the gap but the escape of the flame toward the explosion-proof designated zone Z through the gap can be prevented.

As shown in FIG. 23, the light receiving potion 506 is accommodated in the housing 505. The light receiving portion 506 comprises a photodiode 524, an optical lens 525, and a second light guide 526 as main elements. The photodiode 524 is an example of a light receiving element. The photodiode 524 is mounted on a central portion of the circuit board 517c and directed to the light irradiation hole 514 on the axis O2 of the housing 505.

The optical lens 525 is formed of, for example, glass and has a shape similar to a convex lens. The optical lens 525 is held on the inner peripheral surface of an end portion of the support body 509 so as to face the photodiode 524.

The second light guide 526 is formed of, for example, a columnar, colorless and transparent glass. The second light guide 526 has a flat light emitting surface 528 facing the optical lens 525 and a flat light receiving surface 529 exposed to the designated explosion-proof zone Z through the light incident hole 514. The light emitting surface 528 and the light receiving surface 529 are separated from each other in the axial direction of the second light guide 526.

According to the present embodiment, the second light guide 526 is coaxially held in the support body 509 via a second holder 530. More specifically, the second holder 530 is formed of, for example, a metal material such as an aluminum alloy. The second holder 530 comprises a cylindrical portion 531 in which the second light guide 526 is coaxially fitted and a flange portion 532 formed on one end of the cylindrical portion 531. The flange portion 532 expands to the outside of the radial direction of the cylindrical portion 531.

The cylindrical portion 531 is screwed into the inside of the support body 509 from the direction of the main body 508. A tip of the cylindrical portion 531 on the side opposite to the flange portion 532 and an outer peripheral portion of the light receiving surface 529 of the second light guide 526 abut on the stopper portion 513 of the support body 509, by this screwing. Simultaneously, the flange portion 532 abuts on a step portion 509a of the inner peripheral surface of the support body 509. As a result, the second light guide 526 is held at a fixed position inside the support body 509.

As shown in FIG. 23, the light emitting surface 528 of the second light guide 526 faces the optical lens 525, and the light receiving surface 529 of the second light guide 526 is exposed to the designated explosion-proof zone Z through the light irradiation hole 514, in a state where the second light guide 526 is held inside the support body 509.

According to this embodiment, the light emitting surface 528 of the second light guide 526 is covered with a polarizer 534. The polarizer 534 is, for example, a disc-like element composed of polarizing glass and a polarizing film, and is held inside the support body 509 via a fixing ring 535. The fixing ring 535 is inserted into the support body 509 from the direction of the main body 508 and the outer peripheral portion of the polarizer 534 is sandwiched between the fixing ring 535 and the flange portion 532 of the first holder 530.

Further, a heater 536 for prevention of dew condensation prevention is disposed inside the fixing ring 535. The heater 536 is an element for preventing the function of the polarizer 534 from decreasing due to dew condensation and is in contact with the polarizer 534. The heater 536 is electrically connected to the circuit board 517c via a lead 537.

As shown in FIG. 23 and FIG. 25, a second gap G7 allowing fitting of the second light guide 526 is provided between the outer peripheral surface of the second light guide 526 and the inner peripheral surface of the cylindrical portion 531 of the second holder 530. The second gap G7 communicates with the circuit accommodation chamber 512 inside the support body 509 and also communicates with the designated explosion-proof zone Z through the light incident hole 514.

As shown in FIG. 25, when the second light guide 526 and the cylindrical portion 531 maintain the coaxiality, the size W7 of the second gap G7 can be restated as a distance from an arbitrary point on the inner peripheral surface of the cylindrical portion 531 to the outer peripheral surface of the second light guide 526 distant from the second light guide 526 in the radial direction. The length L7 along the depth direction of the second gap G7 is equal to the total length of the second light guide 526 from the outer peripheral edge of the light emitting surface 528 of the second light guide 526 to the outer peripheral edge of the light receiving surface 529.

Each of the size W7 and the length L7 of the second gap G7 is set to values conforming to the explosion-proof standard. If the size W7 and the length L7 of the second gap G7 conform to the explosion-proof standard, the flame caused by the explosion in the circuit accommodation chamber 512 may reach the second gap G7 beyond the optical lens 525 and the polarizer 534 but the escape of the flame toward the explosion-proof designated zone Z through the second gap G7 can be prevented.

The size W7 and the length L7 of the second gap G7 are varied according to the gas atmosphere of the designated explosion-proof area Z where the photoelectric smoke sensor 400 is installed, the capacity of the circuit accommodation chamber 512, and the like. Since concrete values of the size W7 and the length L7 of the second gap G7 are the same as the size W6 and the length L6 of the first gap G6 of the light emitting unit 402, their explanations are omitted.

The protective member 507 is an element for protecting the light irradiation hole 514 of the housing 505 and the light receiving surface 529 of the second light guide 526 exposed from the light irradiation hole 514 from the external impact and has strength conforming to the explosion-proof standard. The protective member 507 covers an end portion of the support body 509 at which the light irradiation hole 514 is opened, from the outside. The protective member 507 has an opening portion 538 which faces the light incident hole 514.

According to the present embodiment, the light emitted from the light emitting diode 424 of the light emitting unit 402 passes through the optical lens 425 and the polarizer 434 and then is made incident on the light receiving surface 428 of the first light guide 426, in a state in which the photoelectric smoke sensor 400 is in operation. Part of the light incident on the light receiving surface 428 passes through the inside of the first light guide 426 in the axial direction and the remaining light travels toward the light emitting surface 429 while repeating total reflection on the outer peripheral surface of the first light guide 426.

The light reaching the light emitting surface 429 of the first light guide 426 is irradiated from the light irradiation hole 414 to the designated explosion-proof zone Z. The light irradiated in the designated explosion-proof zone Z is made incident on the light receiving surface 529 of the second light guide 526 from the light incident hole 514 of the light receiving unit 403. Part of the light incident on the light receiving surface 529 passes through the inside of the second light guide 526 in the axial direction and the remaining light travels toward the light emitting surface 528 while repeating total reflection on the outer peripheral surface of the second light guide 526.

The light reaching the light emitting surface 528 passes through the polarizer 534 and the optical lens 525 and is emitted toward the photodiode 524, and the photodiode 524 detects the light. As a result, an electric signal indicating that the light has been detected is sent from the photodiode 524 to the circuit board 517c.

The light emitted by the light emitting unit 402 is guided to the light receiving unit 403 without being disturbed, at an ordinary time at which smoke is not included in the air of the designated explosion-proof zone Z. In contrast, if smoke is included in the air of the designated explosion-proof zone Z, the light emitted by the light emitting unit 402 is scattered by the smoke and the quantity of the light incident on the photodiode 524 of the light receiving unit 403 is reduced. For this reason, an electric signal indicating that the light amount has reduced is sent from the photodiode 524 to the circuit board 517c. The circuit board 517c outputs an electric signal to inform the outside that smoke has occurred in the designated explosion-proof zone Z.

More specifically, an electric signal may be sent to a buzzer provided outside to sound a buzzer or the color of light emitted by the indicator lamp provided outside may be changed.

According to the present embodiment, if combustible gas exists in the designated explosion-proof zone Z the combustible gas may enter the light emitting unit 402 and the light receiving unit 403 since both of the light emitting unit 402 and the light receiving unit 403 are exposed in the designated explosion-proof zone Z.

More specifically, in the light emitting unit 402, the combustible gas cannot be avoided from entering the circuit accommodation chamber 412 in the housing 405 through the gap between the guide hole 421 of the housing 405 and the cable gland 422, the gap between the first flange portion 410 of the main body 408 and the second flange portion 411 of the support body 409, and the first gap G6 between the outer peripheral surface of the first light guide 426 and the inner peripheral surface of the cylindrical portion 431 of the first holder 430.

The combustible gas which has entered the circuit accommodation chamber 412 may cause an explosion, for example, when a spark resulting from a short current generated on the surfaces of the circuit boards 417a, 417b, and 417c or an abnormal high temperature part occurs on the surfaces of the circuit boards 417a, 417b, and 417c.

According to the present embodiment, the housing 405 defining the circuit accommodation chamber 412 can sufficiently withstand the explosion in the circuit accommodation chamber 412 without being damaged since the housing 405 has a pressure-resistant explosion-proof structure. The flame generated by the explosion in the circuit accommodation chamber 412 is therefore confined inside the housing 405 and does not leak out to the designated explosion-proof zone Z.

The flame generated by the explosion in the circuit accommodation chamber 412 is guided to the inside of the cylindrical support body 409, and reaches the first gap G6 between the outer peripheral surface of the first light guide 426 and the inner peripheral surface of the cylindrical portion 431 of the first holder 430 beyond the optical lens 425 and the polarizer 434. The flame which has reached the first gap G6 travels toward the light irradiation hole 414 of the housing 405 through the first gap G6.

According to the present embodiment, the size W6 and the length L6 of the first gap G6 are set to values conforming to the explosion-proof standard. For this reason, the flame which has reached the first gap G6 naturally disappears in the course of traveling through the first gap G6, and ejection of the flame from the first gap G6 toward the light irradiation hole 414 can be avoided.

In contrast, in the light receiving unit 403, too, the combustible gas cannot be avoided from entering the circuit accommodation chamber 512 in the housing 505, similarly to the light emitting unit 402. The combustible gas which has entered the circuit accommodation chamber 512 may cause an explosion, for example, when a spark resulting from a short current generated on the surfaces of the circuit boards 517a, 517b, and 517c or an abnormal high temperature part occurs on the surfaces of the circuit boards 517a, 517b, and 517c.

According to the present embodiment, the housing 505 defining the circuit accommodation chamber 512 can sufficiently withstand the explosion in the circuit accommodation chamber 512 without being damaged since the housing 505 has a pressure-resistant explosion-proof structure. The flame generated by the explosion in the circuit accommodation chamber 512 is therefore confined inside the housing 505 and does not leak out to the designated explosion-proof zone Z.

The flame generated by the explosion in the circuit accommodation chamber 512 is guided to the inside of the cylindrical support body 509, and reaches the second gap G7 between the outer peripheral surface of the second light guide 526 and the inner peripheral surface of the cylindrical portion 531 of the second holder 530 beyond the optical lens 525 and the polarizer 534. The flame which has reached the second gap G7 travels toward the light irradiation hole 514 of the housing 505 through the second gap G7.

According to the present embodiment, the size W7 and the length L7 of the second gap G7 are set to values conforming to the explosion-proof standard. For this reason, the flame which has reached the second gap G7 naturally disappears in the course of traveling through the second gap G7, and ejection of the flame from the second gap G7 toward the light irradiation hole 514 can be avoided.

Thus, according to the present embodiment, the flame generated in the circuit accommodation chamber 412 of the light emitting unit 402 and the circuit accommodation chamber 512 of the light receiving unit 403 does not ignite combustible gas, and the explosion accident in the designated explosion-proof zone Z can be prevented preliminarily.

Furthermore, since the first gap G6 and the second gap G7 do not need to be filled with the sealant formed of resin, inconvenience that the flame generated in the circuit accommodation chambers 412 and 512 through the cracks and holes due to aged deterioration of the sealant may leak out into the designated explosion-proof zone Z can be solved. The flame generated in the circuit accommodation chambers 412 and 512 therefore does not ignite the explosive gas outside the photoelectric smoke sensor 400.

In the Fourth Embodiment, each of the size and length of the first gap between the first light guide and the cylindrical portion of the first holder, and the size and length of the second gap between the second light guide and the cylindrical portion of the second holder is set to a value conforming to the explosion-proof standard but, other than these, each of the gap between the optical lens and the support body and the gap between the polarizer and the support body may be set to a value conforming to the explosion-proof standard.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A photoelectric smoke sensor comprising:
a housing of an explosion-proof structure provided in a designated exposition-proof zone and having a circuit accommodation chamber to accommodate a circuit board;
an inflow chamber provided in the housing and communicating with the designated exposition-proof zone;
a light emitting portion provided in the inflow chamber; and
a light receiving portion provided in the inflow chamber, wherein the light emitting portion includes:
a light emitting element;
a first light guide guiding light emitted by the light emitting element to the inflow chamber; and
a first support portion surrounding and holding the first light guide and communicating with the circuit accommodation chamber, the light receiving portion includes:
a light receiving element;
a second light guide receiving light emitted by the light emitting element in the inflow chamber and guiding the light to the light receiving element; and
a second support portion surrounding and holding the second light guide and communicating with the circuit accommodation chamber, and the first support portion and the second support portion are configured to prevent escape of a flame from the circuit accommodation chamber to the inflow chamber.

2. The photoelectric smoke sensor of claim 1, wherein the first support portion has a first gap communicating with the circuit accommodation chamber and the inflow chamber between the first support portion and an outer peripheral surface of the first light guide, the second support portion has a second gap communicating with the circuit accommodation chamber and the inflow chamber between the second support portion and an outer peripheral surface of the second light guide, and each of sizes of the first gap and the second gap and lengths along a depth direction of the first gap and the second gap is set to a value which prevents escape of the flame from the circuit accommodation chamber to the inflow chamber.

3. The photoelectric smoke sensor of claim 2, wherein each of the sizes of the first gap and the second gap and the lengths of the first gap and the second gap conforms to an explosion-proof standard.

4. The photoelectric smoke sensor of claim 1, wherein the inflow chamber is formed between the housing and a cover covering the housing, and
the cover covers the light emitting portion and the light receiving portion and has a strength conforming to an explosion-proof standard.

5. The photoelectric smoke sensor of claim 4, wherein shielding walls which blocks light entering from the designated exposition-proof zone to the inflow chamber are provided in the inflow chamber,
the shielding walls are covered with the cover, and
a ventilation port communicating with the inflow chamber is formed on the cover.

6. A photoelectric smoke sensor comprising:
a housing of an explosion-proof structure provided in a designated exposition-proof zone and having a circuit accommodation chamber to accommodate a circuit board;
an inflow chamber provided in the housing and communicating with the designated exposition-proof zone;
shielding walls provided on at least an outer peripheral portion of the inflow chamber and blocking light entering from the designated exposition-proof zone to the inflow chamber;
a light emitting portion provided in the inflow chamber, and having a first light guide guiding light emitted by the light emitting element to a central portion of the inflow chamber surrounded the shielding walls and a first support portion surrounding and holding the first light guide and communicating with the circuit accommodation chamber; and a light receiving portion provided in the inflow chamber, and having a second light guide receiving light emitted by the light emitting element in the inflow chamber and guiding the light to the light receiving element and a second support portion surrounding and holding the second light guide and communicating with the circuit accommodation chamber;

a cover continuously covering the shielding walls, the light emitting portion, and the light receiving portion, and having a ventilation port which communicates with the inflow chamber opened to an outer peripheral wall surrounding the shielding walls; and at least one guide wall provided between the outer peripheral wall of the cover and the shielding walls, and guiding an air flow moving from the ventilation port to the shielding walls, to a central portion of the inflow chamber through an interval between the adjacent shielding walls, wherein the first support portion and the second support portion are configured to prevent escape of a flame from the circuit accommodation chamber to the inflow chamber.

7. The photoelectric smoke sensor of claim 6, wherein
the first support portion has a first gap communicating with the circuit accommodation chamber and the inflow chamber between the first support portion and an outer peripheral surface of the first light guide, the second support portion has a second gap communicating with the circuit accommodation chamber and the inflow chamber between the second support portion and an outer peripheral surface of the second light guide, and each of sizes of the first gap and the second gap and lengths along a depth direction of the first gap and the second gap is set to a value which prevents escape of the flame from the circuit accommodation chamber to the inflow chamber.

8. The photoelectric smoke sensor of claim 7, wherein
each of the sizes of the first gap and the second gap and the lengths of the first gap and the second gap conforms to an explosion-proof standard.

9. The photoelectric smoke sensor of claim 6, wherein
the guide wall extends to the central portion of the inflow chamber, at an outer peripheral portion of the inflow chamber.

10. A photoelectric smoke sensor comprising:
a housing of an explosion-proof structure provided in a designated exposition-proof zone and having a circuit accommodation chamber to accommodate a circuit board; and an optical unit supported by the housing, wherein the optical unit includes:

a light guide through which light passes; and a support portion surrounding and holding the light guide and communicating with the circuit accommodation chamber, and the support portion is configured to prevent escape of a flare from the circuit accommodation chamber to the inflow chamber.

11. The photoelectric smoke sensor of claim 10, wherein
a gap communicating with the circuit accommodation chamber and the inflow chamber is formed between the support portion and the light guide, and a sizes of the gap and a length along a depth direction of the gap are set to values which prevent escape of the flame from the circuit accommodation chamber to an outside of the housing through the gap.

12. The photoelectric smoke sensor of claim 11, wherein
the size and length of the gap conform to an explosion-proof standard.

* * * * *